United States Patent
Farias-Eisner et al.

(10) Patent No.: US 9,241,976 B2
(45) Date of Patent: Jan. 26, 2016

(54) USE OF HDL-RELATED MOLECULES TO TREAT AND PREVENT PROINFLAMMATORY CONDITIONS

(75) Inventors: Robin Farias-Eisner, Calabasas, CA (US); Srinivasa T. Reddy, Cerritos, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/239,530

(22) PCT Filed: Aug. 29, 2012

(86) PCT No.: PCT/US2012/052925
§ 371 (c)(1),
(2), (4) Date: Feb. 18, 2014

(87) PCT Pub. No.: WO2013/033260
PCT Pub. Date: Mar. 7, 2013

(65) Prior Publication Data
US 2014/0323410 A1    Oct. 30, 2014

Related U.S. Application Data

(60) Provisional application No. 61/528,447, filed on Aug. 29, 2011, provisional application No. 61/646,772, filed on May 14, 2012, provisional application No. 61/624,333, filed on Apr. 15, 2012.

(51) Int. Cl.
C07K 14/775 (2006.01)
A61K 38/17 (2006.01)
A61K 38/16 (2006.01)

(52) U.S. Cl.
CPC ............. *A61K 38/1709* (2013.01); *A61K 38/16* (2013.01); *C07K 14/775* (2013.01)

(58) Field of Classification Search
CPC ... C07K 14/775; A61K 38/16; A61K 38/1709
See application file for complete search history.

(56) References Cited

U.S. PATENT DOCUMENTS

| | | | |
|---|---|---|---|
| 5,114,863 A | 5/1992 | McCombs et al. | |
| 5,891,641 A | 4/1999 | Prusiner et al. | |
| 5,955,582 A | 9/1999 | Newman et al. | |
| 7,191,068 B2 | 3/2007 | Rosenfeld et al. | |
| 7,291,461 B2 | 11/2007 | Welch et al. | |
| 7,427,662 B2 | 9/2008 | Hornick et al. | |
| 7,510,842 B2 | 3/2009 | Fung et al. | |
| 7,510,881 B2 | 3/2009 | Ramael et al. | |
| 7,575,876 B2 | 8/2009 | Zhang | |
| 7,589,174 B2 | 9/2009 | Argon et al. | |
| 7,604,948 B2 | 10/2009 | Amaral et al. | |
| 7,605,003 B2 | 10/2009 | Chan et al. | |
| 7,670,792 B2 | 3/2010 | Farias-Eisner et al. | |
| 7,723,045 B2 | 5/2010 | Fogelman et al. | |
| 7,723,303 B2 | 5/2010 | Fogelman et al. | |
| 7,947,645 B2 * | 5/2011 | Vitek et al. | 514/1.1 |
| 8,323,915 B2 | 12/2012 | Farias-Eisner et al. | |
| 2003/0027216 A1 | 2/2003 | Kiernan et al. | |
| 2003/0191057 A1 | 10/2003 | Fogelman et al. | |
| 2005/0059013 A1 | 3/2005 | Chan et al. | |
| 2005/0214760 A1 | 9/2005 | Chan et al. | |
| 2006/0068405 A1 | 3/2006 | Diber et al. | |
| 2006/0094039 A1 | 5/2006 | Rosenfeld et al. | |
| 2006/0257866 A1 | 11/2006 | Welch et al. | |
| 2007/0031379 A1 | 2/2007 | Lee et al. | |
| 2009/0246769 A1 | 10/2009 | Sato et al. | |
| 2010/0081151 A1 | 4/2010 | Farias-Eisner et al. | |
| 2010/0173788 A1 | 7/2010 | Goncalves et al. | |
| 2010/0227825 A1 * | 9/2010 | Fogelman et al. | 514/13 |
| 2011/0027894 A1 | 2/2011 | Farias-Eisner et al. | |
| 2012/0245101 A1 * | 9/2012 | Anantharamaiah et al. | 514/19.3 |
| 2013/0090256 A1 | 4/2013 | Farias-Eisner et al. | |

FOREIGN PATENT DOCUMENTS

| | | | |
|---|---|---|---|
| EP | 0201187 A1 | 11/1986 | |
| EP | 1789805 B1 | 9/2010 | |
| EP | 2199801 B1 | 5/2013 | |
| WO | WO9108488 A1 | 6/1991 | |
| WO | WO2004012588 A2 | 2/2004 | |
| WO | WO2004013609 A2 | 2/2004 | |
| WO | WO2005093413 A2 | 10/2005 | |
| WO | WO2006063132 A2 | 6/2006 | |
| WO | WO2006099126 A2 | 9/2006 | |
| WO | WO2007068985 A2 | 6/2007 | |
| WO | WO 2008156873 A2 * | 12/2008 | A61K 38/10 |
| WO | WO2009032693 A2 | 3/2009 | |
| WO | WO2009073725 A2 | 6/2009 | |
| WO | WO2012047930 A2 | 4/2012 | |

OTHER PUBLICATIONS

Lawrence W. Castellani, ApoA-II Versus ApoA-I: Two for One Is Not Always a Good Deal, Arterioscler Thromb Vasc Biol. 2001;21:1870-1872.*

(Continued)

*Primary Examiner* — Julie Ha
*Assistant Examiner* — Erinne Dabkowski
(74) *Attorney, Agent, or Firm* — Karen S. Canady; canady + lortz LLP

(57) ABSTRACT

Molecules and compositions are described for use in the treatment and prevention of pro-inflammatory conditions. HDL-related molecules, including ApoA-I, bovine HDL and HDL mimetics, in particular, are demonstrated to prevent UV-induced cell death and oxidative stress in skin cells and to inhibit tumor growth and development in a variety of cancers. HDL-related molecules can be used as an oral supplement and in other compositions to prevent or treat pro-inflammatory skin conditions and systemic proinflammatory conditions, including Alzheimer's disease and various cancers.

11 Claims, 19 Drawing Sheets

(56) References Cited

OTHER PUBLICATIONS

Mohamad Navab, Oral Administration of an Apo A-I Mimetic Peptide Synthesized From D-Amino Acids, Dramatically Reduces Atherosclerosis in Mice Independent of Plasma Cholesterol, Circulation. 2002;105:290-292.*
MSDS f or High Density Lipoprotein (HDL), Bov ine Serum, Lee Biosolutions, 2009.*
Merck Manuals Brain Tumors accessed Oct. 27, 2014 at URL merckmanuals.com/home/brain_spinal_cord_and_nerve_disorders/tumors_of_the_nervous_system/brain_tumors.html.*
Merck Manual Colorectal Cancer accessed Oct. 27, 2014 at URL merckmanuals.com/home/skin_disorders/skin_cancers/melanoma.html?qt=melanoma&alt=sh).*
Merck Manual Breast Cancer accessed Oct. 27, 2014 at URL: merckmanuals.com/home/womens_health_issues/breast_disorders/breast_cancer.html.*
Merck Manual Ovarian Cancer, accessed Oct. 27, 2014 at merckmanuals.com/home/womens_health_issues/cancers_of_the_female_reproductive_system/ovarian_cancer.html.*
Merck Manual Thyroid Cancers, accessed Oct. 27, 2014, merckmanuals.com/professional/endocrine_and_metabolic_disorders/thyroid_disorders/thyroid_cancers.html.*
Feng Su, Apolipoprotein A-I (apoA-I) and apoA-I mimetic peptides inhibit tumor development in a mouse model of ovarian cancer, PNAS, Nov. 16, 2010, vol. 107, No. 46, pp. 19997-20002.*
Duk, J.M. et al., "CA 125: A useful marker in endometrial carcinoma", 1986, Amer J. of Obstetrics and Gynecology, 155(5): 1097-1102. 1 page Abstract.
Kozak, Katherine R., "Characterization of serum biomarkers for detection of early stage ovarian cancer", Proteomics, 2005, 5: 4589-4596.
Kozak, Katherine R., "Identification of biomarkers for ovarian cancer . . . prognosis", PNAS, Oct. 14, 2003, 100(21): 12343-12348.
Lo, S.S.T. et al., "Prognostic Significance of Tumour Markers in Endometrial Cancer", 1997, Tumor Biology, 18:241-249.
Munstedt, Karsten, "Impact of hemoglobin levels before and during chemotherapy . . . cancer", Int'l. Journal of Oncology, 2003, 23: 837-843.
Obermair, Andreas, "The relationship of pretreatment serum hemoglobin level . . . patients", 1998, American Cancer Society, XP008056584, pp. 726-731.
Rai, Alex J., "Proteomic approaches to tumor marker discovery", Dec. 2002, Arch Pathol Lab Med, vol. 126, pp. 1518-1526.
Su, Feng et al., "Validation of candidate serum ovarian cancer biomarkers for early detection", Biomarker Insights, 2007, 2: 369-375.
Tockman, M. et al., "Considerations in Bringing a Cancer Biomarker to Clinical Application", Cancer Research, 1992, 52:2711s-2718s.
Tosner, J., "Serum prealbumin, transferrin and alpha-1-acid glycoprotein in patients with gynecological carcinomas", 1988, Neoplasma, Sciences, 35(4):403-412.
Van Belle, S.J.-P, What is the value of hemoglobin as a prognostic and predictive factor in cancer?, 2004, EJC Supplements, XP008056585, 2(2): 11-19.
Zhang, Zhen, "Protein identification and immunoassay evaluation of a panel of biomarkers . . . ovarian cancer", AACR Meeting Abstracts Online, 2004, 45: Abstract #1063.
Extended European Search Report, EP Application No. 10003541.9, Jul. 28, 2010.
Extended European Search Report, EP Application No. 10009544.7, Sep. 5, 2011, 10 pp.
EPO Office Action dated Jul. 9, 2012, in EP App. No. 10009544.7-1223.
EPO Office Action Response as filed on Apr. 3, 2012, in EP App. No. 10009544.7-1223.
International Search Report + Written Opinion dated Apr. 27, 2012 in PCT Application No. PCT/US2011/054817, filed Oct. 4, 2011.
Quest Diagnostics OVA1 16991, Test Overview, Valencia, CA, 2009, www.questdiagnostics.com.
USPTO Office Action mailed on Oct. 11, 2012 in U.S. Appl. No. 12/860,293, filed Aug. 20, 2010.
Datta G. et al: "Anti-inflammatory and recycling properties of an apolipoprotein mimetic peptide, Ac—hE18A—NH2", Atherosclerosis, Elsevier Ireland LTD, IE, vol. 208, No. 1, Jan. 1, 2010, pp. 134-141, XP026834433, ISSN: 0021-9150
Ganapathy E. et al: "D-4F an apoA-I mimetic peptide inhibits proliferation and tumorigenicity of epithelial ovarian cancer cells by upregulating the antioxidant enzyme MnSOD", International Journal of Cancer, vol. 130, No. 5, Mar. 21, 2011, pp. 1071-1081, XP009168920, ISSN: 1097-0215
Gao F. et al: "L-5F, an apolipoprotein A-I mimetic, inhibits tumor angiogenesis by suppressing VEGF/basic FGF signaling pathways." Apr. 2011, Integrative Biology: Quantitative Biosciences From Nano to Macro Apr. 2011, vol. 3, NR. 4, pp. 479-489, XP002736375, ISSN: 1757-9708
Imaizumi S. et al: "Dysfunctional high-density lipoprotein and the potential of apolipoprotein A-1 Mimetic peptides to normalize the composition and function of lipoproteins.", May 28, 2011, Circulation Journal : Official Journal of the Japanese Circulation Society 2011, vol. 75, NR. 7, p. 1533-1538, XP002736376, ISSN: 1347-4820
Navab M. et al: "Anovel method for oral delivery of apolipoprotein mimetic peptides synthesized from all L-amino acids", The Journal of Lipid Research, vol. 50, No. 8, Aug. 1, 2009, pp. 1538-1547, XP055056762, ISSN: 0022-2275, DOI: 10.1194/jlr.M800539-JLR200.
Nayyar G. et al: "Sidedness of interfacial arginine residues and antiatherogenicity of apolipoprotein A-I mimetic peptides", The Journal of Lipid Research, vol. 53, No. 5, Feb. 29, 2012, pp. 849-858, XP055171334, ISSN: 0022-2275, DOI: 10.1194jjlr.M019844
Sharifov O. et al: "Apolipoprotein E mimetics and cholesterol-lowering Properties", American Journal of Cardiovascular Drugs, ADIS International, NZ, vol. 11, No. 6, Dec. 1, 2011, pp. 371-381, XP009182740, ISSN: 1175-3277, DOI: 10.2165/11594190-000000000-00000.
Su F. et al: "Apolipoprotein A-I (apoA-I) and apoA-I mimetic peptides inhibit tumor development in a mouse model of ovarian cancer", Proceedings of the National Academy of Sciences, vol. 107, No. 46, Nov. 1, 2010, pp. 19997-20002, XP055095580, ISSN: 0027-8424, DOI: 10.1073fpnas.1009010107.
Extended European Search Report for corresponding EP Application 12826789.5 (EP2751126), dated Mar. 10, 2015.

* cited by examiner

A
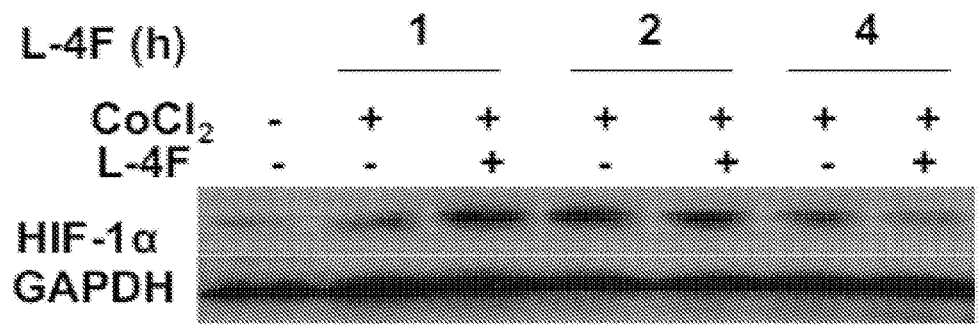
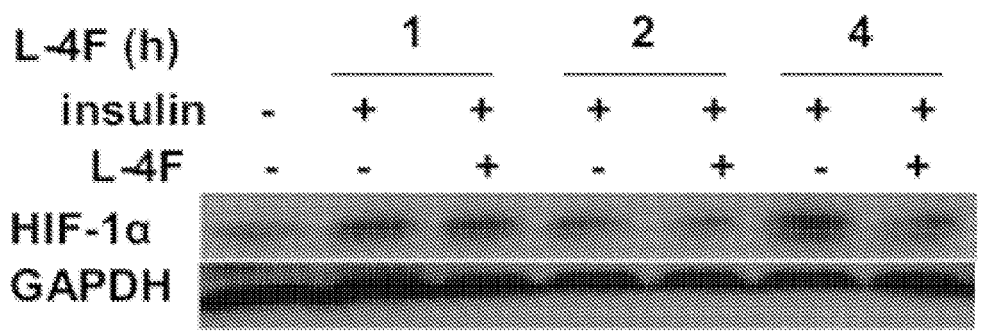
C
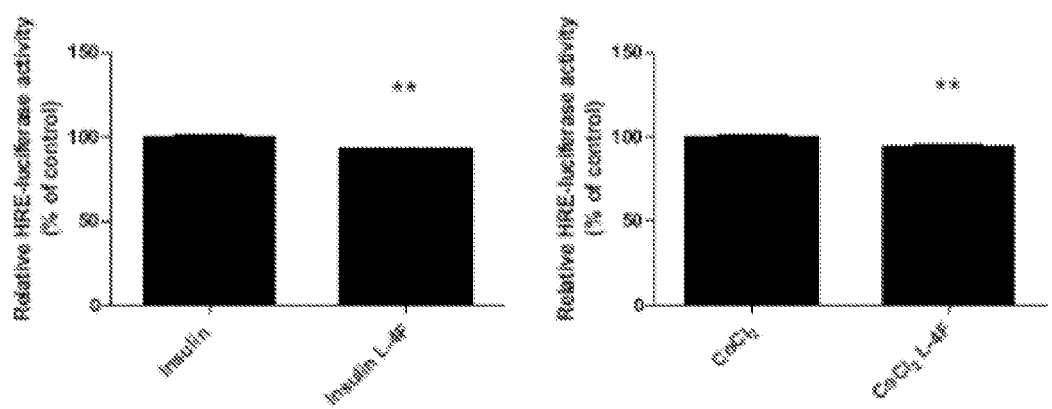
Figures 9A and 9C

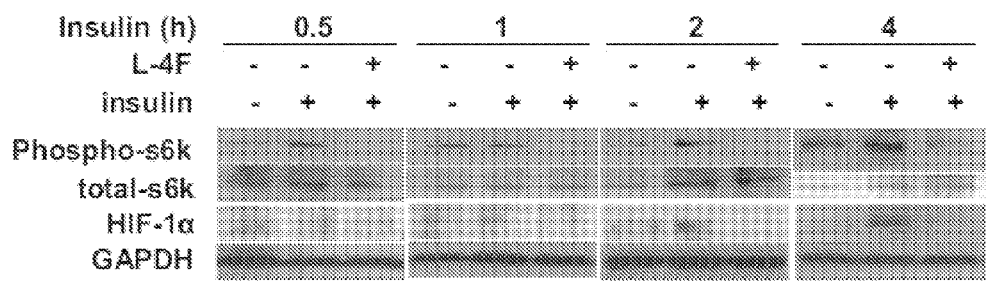
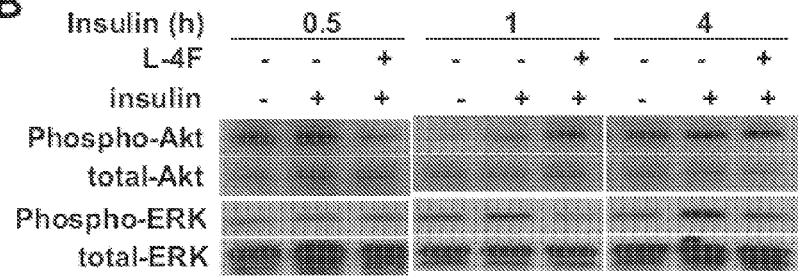
Figures 10A and 10B
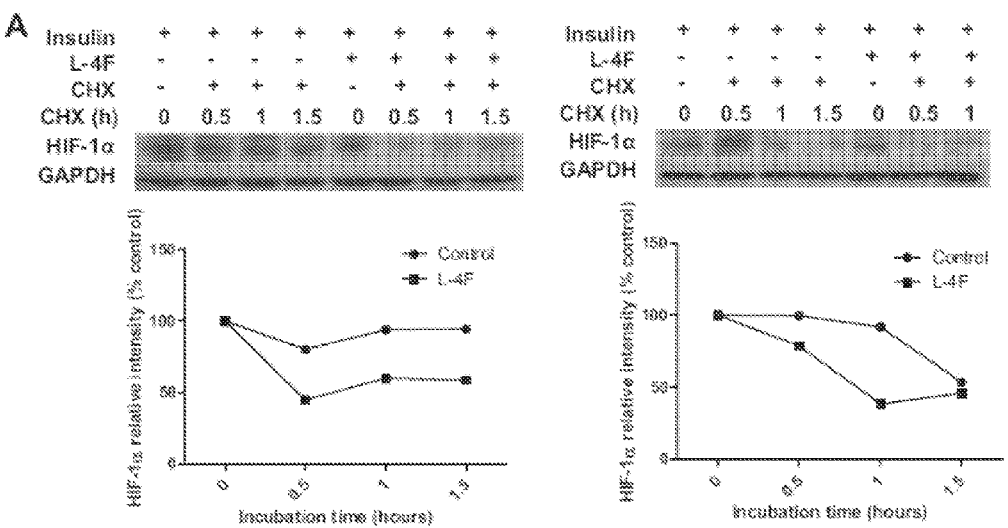
Figure 11A

SEQUENCE LISTING

```
<160> NUMBER OF SEQ ID NOS: 28

<210> SEQ ID NO 1
<211> LENGTH: 20
<212> TYPE: PRT
<213> ORGANISM: Artificial Sequence
<220> FEATURE:
```

```
<223> OTHER INFORMATION: synthetic peptide mimetic

<400> SEQUENCE: 1

Leu Arg Lys Leu Arg Lys Arg Leu Leu Arg Leu Val Gly Arg Gln Leu
1               5                   10                  15

Glu Glu Phe Leu
            20

<210> SEQ ID NO 2
<211> LENGTH: 28
<212> TYPE: PRT
<213> ORGANISM: Artificial Sequence
<220> FEATURE:
<223> OTHER INFORMATION: synthetic peptide mimetic

<400> SEQUENCE: 2

Leu Arg Lys Leu Arg Lys Arg Leu Leu Arg Asp Trp Leu Lys Ala Phe
1               5                   10                  15

Tyr Asp Lys Val Ala Glu Lys Leu Lys Glu Ala Phe
            20                  25

<210> SEQ ID NO 3
<211> LENGTH: 28
<212> TYPE: PRT
<213> ORGANISM: Artificial Sequence
<220> FEATURE:
<223> OTHER INFORMATION: synthetic peptide mimetic
<220> FEATURE:
<221> NAME/KEY: MOD_RES
<222> LOCATION: (15)..(15)
<223> OTHER INFORMATION: Aib

<400> SEQUENCE: 3

Leu Arg Lys Leu Arg Lys Arg Leu Leu Arg Asp Trp Leu Lys Ala Phe
1               5                   10                  15

Tyr Asp Lys Val Ala Glu Lys Leu Lys Glu Ala Phe
            20                  25

<210> SEQ ID NO 4
<211> LENGTH: 28
<212> TYPE: PRT
<213> ORGANISM: Artificial Sequence
<220> FEATURE:
<223> OTHER INFORMATION: synthetic peptide mimetic
<220> FEATURE:
<221> NAME/KEY: MOD_RES
<222> LOCATION: (21)..(21)
<223> OTHER INFORMATION: Aib

<400> SEQUENCE: 4

Leu Arg Lys Leu Arg Lys Arg Leu Leu Arg Asp Trp Leu Lys Ala Phe
1               5                   10                  15

Tyr Asp Lys Val Ala Glu Lys Leu Lys Glu Ala Phe
            20                  25

<210> SEQ ID NO 5
<211> LENGTH: 28
<212> TYPE: PRT
<213> ORGANISM: Artificial Sequence
<220> FEATURE:
<223> OTHER INFORMATION: synthetic peptide mimetic
<220> FEATURE:
<221> NAME/KEY: MOD_RES
<222> LOCATION: (27)..(27)
<223> OTHER INFORMATION: Aib

<400> SEQUENCE: 5
```

```
Leu Arg Lys Leu Arg Lys Arg Leu Leu Arg Asp Trp Leu Lys Ala Phe
1               5                   10                  15

Tyr Asp Lys Val Ala Glu Lys Leu Lys Glu Ala Phe
            20                  25
```

<210> SEQ ID NO 6
<211> LENGTH: 28
<212> TYPE: PRT
<213> ORGANISM: Artificial Sequence
<220> FEATURE:
<223> OTHER INFORMATION: syntheitc peptide mimetic
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (21)..(21)
<223> OTHER INFORMATION: Aib

<400> SEQUENCE: 6

```
Leu Arg Lys Leu Arg Lys Arg Leu Leu Arg Asp Trp Leu Lys Ala Phe
1               5                   10                  15

Tyr Asp Lys Val Ala Glu Lys Leu Lys Glu Ala Phe
            20                  25
```

<210> SEQ ID NO 7
<211> LENGTH: 28
<212> TYPE: PRT
<213> ORGANISM: Artificial Sequence
<220> FEATURE:
<223> OTHER INFORMATION: synthetic peptide mimetic
<220> FEATURE:
<221> NAME/KEY: MOD_RES
<222> LOCATION: (21)..(21)
<223> OTHER INFORMATION: Aib
<220> FEATURE:
<221> NAME/KEY: MOD_RES
<222> LOCATION: (27)..(27)
<223> OTHER INFORMATION: Aib

<400> SEQUENCE: 7

```
Leu Arg Lys Leu Arg Lys Arg Leu Leu Arg Asp Trp Leu Lys Ala Phe
1               5                   10                  15

Tyr Asp Lys Val Ala Glu Lys Leu Lys Glu Ala Phe
            20                  25
```

<210> SEQ ID NO 8
<211> LENGTH: 28
<212> TYPE: PRT
<213> ORGANISM: Artificial Sequence
<220> FEATURE:
<223> OTHER INFORMATION: synthetic peptide mimetic
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (27)..(27)
<223> OTHER INFORMATION: Aib

<400> SEQUENCE: 8

```
Leu Arg Lys Leu Arg Lys Arg Leu Leu Arg Asp Trp Leu Lys Ala Phe
1               5                   10                  15

Tyr Asp Lys Val Ala Glu Lys Leu Lys Glu Ala Phe
            20                  25
```

-continued

```
<210> SEQ ID NO 9
<211> LENGTH: 28
<212> TYPE: PRT
<213> ORGANISM: Artificial Sequence
<220> FEATURE:
<223> OTHER INFORMATION: synthetic peptide mimetic
<220> FEATURE:
<221> NAME/KEY: MOD_RES
<222> LOCATION: (15)..(15)
<223> OTHER INFORMATION: Aib
<220> FEATURE:
<221> NAME/KEY: MOD_RES
<222> LOCATION: (21)..(21)
<223> OTHER INFORMATION: Aib
<220> FEATURE:
<221> NAME/KEY: MOD_RES
<222> LOCATION: (27)..(27)
<223> OTHER INFORMATION: Aib

<400> SEQUENCE: 9

Leu Arg Lys Leu Arg Lys Arg Leu Leu Arg Asp Trp Leu Lys Ala Phe
1               5                   10                  15

Tyr Asp Lys Val Ala Glu Lys Leu Lys Glu Ala Phe
            20                  25

<210> SEQ ID NO 10
<211> LENGTH: 267
<212> TYPE: PRT
<213> ORGANISM: Artificial Sequence
<220> FEATURE:
<223> OTHER INFORMATION: synthetic peptide mimetic

<400> SEQUENCE: 10

Met Lys Ala Ala Val Leu Thr Leu Ala Val Leu Gly Lys Gln Leu
1               5                   10                  15

Asn Leu Lys Leu Val Gln Pro Tyr Leu Asp Asp Phe Gln Lys Asp Ala
            20                  25                  30

Leu Arg Thr His Leu Ala Pro Tyr Gly Leu Leu Pro Val Leu Glu Ser
        35                  40                  45

Phe Lys Leu Phe Leu Thr Gly Ser Gln Ala Arg His Leu Asp Asn Trp
    50                  55                  60

Asp Ser Val Thr Ser Thr Lys Trp Gln Glu Glu Met Glu Leu Tyr Arg
65                  70                  75                  80

Ser Asp Glu Leu Arg Gln Arg Leu Ala Ala Val Ser Phe Leu Ser Ala
                85                  90                  95

Leu Glu Glu Tyr Phe Trp Gln Gln Asp Glu Pro Pro Gln Ser Phe Ser
            100                 105                 110

Lys Leu Arg Glu Gln Leu Gly Pro Gln Lys Val Glu Pro Leu Arg Ala
        115                 120                 125

Glu Leu Arg Leu Glu Ala Leu Lys Glu Asn Gly Gly Thr Lys Lys Leu
    130                 135                 140

Asn Thr Gln Pro Trp Asp Arg Val Lys Asp Leu Ala Thr Val Thr Gln
145                 150                 155                 160

Glu Phe Trp Asp Asn Leu Glu Gln Glu Gly Ala Arg Gln Lys Leu His
                165                 170                 175

Glu Ala Arg Leu Ala Glu Tyr His Ala Lys Ala Val Tyr Val Asp Val
            180                 185                 190

Leu Lys Asp Ser Gly Lys Glu Thr Glu Gly Leu Arg Gln Glu Met Leu
        195                 200                 205

Gln Glu Lys Leu Ser Pro Leu Gly Glu Thr His Leu Ser Thr Leu
    210                 215                 220
```

```
Ser Glu Lys Arg Asp Tyr Val Ser Gln Phe Glu Gly Ser Lys Asp
225                 230                 235                 240

Leu Glu Glu Val Lys Ala Lys Glu Met Arg Asp Arg Ala Arg Ala His
                245                 250                 255

Val Ala Lys Pro Ala Leu Glu Asp Leu Arg Gln
            260                 265
```

<210> SEQ ID NO 11
<211> LENGTH: 243
<212> TYPE: PRT
<213> ORGANISM: Artificial Sequence
<220> FEATURE:
<223> OTHER INFORMATION: synthetic peptide mimetic

<400> SEQUENCE: 11

```
Asp Glu Pro Pro Gln Ser Pro Trp Asp Arg Val Lys Asp Leu Ala Thr
1               5                   10                  15

Val Tyr Val Asp Val Leu Lys Asp Ser Gly Arg Asp Tyr Val Ser Gln
            20                  25                  30

Phe Glu Gly Ser Ala Leu Gly Lys Gln Leu Asn Leu Lys Leu Leu Asp
            35                  40                  45

Asn Trp Asp Ser Val Thr Ser Thr Phe Ser Lys Leu Arg Glu Gln Leu
50                  55                  60

Gly Pro Val Thr Gln Glu Phe Trp Asp Asn Leu Glu Lys Glu Thr Glu
65                  70                  75                  80

Gly Leu Arg Gln Glu Met Ser Lys Asp Leu Glu Glu Val Lys Ala Lys
                85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
    130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Arg Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Arg Gln Gly Leu Leu Pro Val Leu Glu Ser
    210                 215                 220

Phe Lys Val Ser Phe Leu Ser Ala Leu Glu Glu Tyr Thr Lys Lys Leu
225                 230                 235                 240

Asn Thr Gln
```

<210> SEQ ID NO 12
<211> LENGTH: 18
<212> TYPE: PRT
<213> ORGANISM: Artificial Sequence
<220> FEATURE:
<223> OTHER INFORMATION: synthetic peptide mimetic

<400> SEQUENCE: 12

```
Asp Trp Phe Lys Ala Phe Tyr Asp Lys Val Ala Glu Lys Phe Lys Glu
1               5                   10                  15
```

```
<210> SEQ ID NO 13
<211> LENGTH: 18
<212> TYPE: PRT
<213> ORGANISM: Artificial Sequence
<220> FEATURE:
<223> OTHER INFORMATION: synthetic peptide mimetic

<400> SEQUENCE: 13

Asp Trp Phe Ala Lys Asp Tyr Phe Lys Lys Ala Phe Val Glu Glu Phe
1               5                   10                  15
Ala Lys

<210> SEQ ID NO 14
<211> LENGTH: 18
<212> TYPE: PRT
<213> ORGANISM: Artificial Sequence
<220> FEATURE:
<223> OTHER INFORMATION: synthetic peptide mimetic
<220> FEATURE:
<221> NAME/KEY: MOD_RES
<222> LOCATION: (11)..(11)
<223> OTHER INFORMATION: Aib
<220> FEATURE:
<221> NAME/KEY: MOD_RES
<222> LOCATION: (17)..(17)
<223> OTHER INFORMATION: Aib

<400> SEQUENCE: 14

Asp Trp Phe Lys Ala Phe Tyr Asp Lys Val Ala Glu Lys Phe Lys Glu
1               5                   10                  15
Ala Phe

<210> SEQ ID NO 15
<211> LENGTH: 10
<212> TYPE: PRT
<213> ORGANISM: Artificial Sequence
<220> FEATURE:
<223> OTHER INFORMATION: synthetic peptide mimetic

<400> SEQUENCE: 15

Leu Arg Lys Leu Arg Lys Arg Leu Leu Arg
1               5                   10

<210> SEQ ID NO 16
<211> LENGTH: 22
<212> TYPE: DNA
<213> ORGANISM: Artificial Sequence
<220> FEATURE:
<223> OTHER INFORMATION: primer

<400> SEQUENCE: 16
tccagttacg ttccttcgat ca                                              22

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
tttgaggact tgcgctttca                                                 20
```

```
<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
cggcgaagag aagagacaca                                              20

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
ggaggaaggt caaccactca                                              20

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
cgggccaaga gtgtgctaaa                                              20

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
tgacgatacc ggagccaatg                                              20

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
tgctactacc agcaccatgc                                              20

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
atgctcccag tggactcatc                                              20

<210> SEQ ID NO 24
<211> LENGTH: 21
<212> TYPE: DNA
<213> ORGANISM: Artificial Sequence
<220> FEATURE:
<223> OTHER INFORMATION: primer
```

```
<400> SEQUENCE: 24
ggaaggtgaa ggtcggagtc a                                              21

<210> SEQ ID NO 25
<211> LENGTH: 25
<212> TYPE: DNA
<213> ORGANISM: Artificial Sequence
<220> FEATURE:
<223> OTHER INFORMATION: primer

<400> SEQUENCE: 25
gtcattgatg gcaacaatat ccact                                          25

<210> SEQ ID NO 26
<211> LENGTH: 10
<212> TYPE: PRT
<213> ORGANISM: Artificial Sequence
<220> FEATURE:
<223> OTHER INFORMATION: synthetic peptide mimetic

<400> SEQUENCE: 26

Leu Val Gly Arg Gln Leu Glu Glu Phe Leu
1               5                   10

<210> SEQ ID NO 27
<211> LENGTH: 18
<212> TYPE: PRT
<213> ORGANISM: Artificial Sequence
<220> FEATURE:
<223> OTHER INFORMATION: synthetic peptide mimetic

<400> SEQUENCE: 27

Asp Trp Phe Arg Ala Phe Tyr Asp Lys Val Ala Glu Lys Phe Arg Glu
1               5                   10                  15

Ala Phe

<210> SEQ ID NO 28
<211> LENGTH: 18
<212> TYPE: PRT
<213> ORGANISM: Artificial Sequence
<220> FEATURE:
<223> OTHER INFORMATION: synthetic peptide mimetic
<220> FEATURE:
<221> NAME/KEY: MOD_RES
<222> LOCATION: (11)..(11)
<223> OTHER INFORMATION: Aib
<220> FEATURE:
<221> NAME/KEY: MOD_RES
<222> LOCATION: (17)..(17)
<223> OTHER INFORMATION: Aib

<400> SEQUENCE: 28

Asp Trp Phe Arg Ala Phe Tyr Asp Lys Val Ala Glu Lys Phe Arg Glu
1               5                   10                  15

Ala Phe
```

USE OF HDL-RELATED MOLECULES TO TREAT AND PREVENT PROINFLAMMATORY CONDITIONS

This application claims the benefit of U.S. provisional patent application 61/646,772, filed May 14, 2012, 61/624,333, filed Apr. 15, 2012, and 61/528,447, filed Aug. 29, 2011, the entire contents of each of which are incorporated herein by reference.

This application is related to U.S. provisional patent application No. 61/389,618, filed Oct. 4, 2010, and to U.S. patent application Ser. No. 12/860,293, filed Aug. 20, 2010, which is a continuation-in-part of application Ser. No. 12/630,458, filed Dec. 3, 2009, which is a divisional of application Ser. No. 11/571,986, filed Jul. 18, 2007, now U.S. Pat. No. 7,670,792, which is a national stage filing under 35 U.S.C. §371 of PCT/US2005/024985, filed Jul. 14, 2005, which claims the benefit of U.S. provisional patent application No. 60/674,489, filed Apr. 25, 2005, and 60/588,007, filed Jul. 14, 2004, the entire contents of each of which are incorporated herein by reference.

Throughout this application various publications are referenced. The disclosures of these publications in their entireties are hereby incorporated by reference into this application in order to describe more fully the state of the art to which this invention pertains.

TECHNICAL FIELD OF THE INVENTION

The present invention relates generally to prevention and treatment of proinflammatory conditions and cancer through the use of HDL-related molecules. The invention is more specifically related to apolipoprotein A-I (ApoA-I), HDL, and HDL mimetics, and their use in preventing and treating proinflammatory conditions, including skin and systemic proinflammatory conditions, particularly epithelial cancers as well as Alzheimer's disease, inflammatory skin diseases, inflammatory bowel disease, and inflammatory diseases associated with aging. Molecules, including full-length ApoA-I protein, HDL, antibodies and antisense/interference nucleotides that modulate and/or mimic the expression and/or function of these targets can be used in oral supplements, vaccines and pharmaceutical compositions for the treatment of various conditions, alone or in combination with other anti-oxidants.

BACKGROUND OF THE INVENTION

Proinflammation is a widespread phenomenon that has strong association with stress and is connected with various diseases. Proinflammatory activities in general are initiated to overcome infection or invasion of potentially deleterious biological agents (bacteria, viruses, parasites etc.). While fighting invasion, proinflammation has beneficial and deteriorating capacities and can exert detrimental effects. The sequelae of an unbalanced systemic inflammatory reaction include derangement of microcirculation, shock, transudation into organs and defects of coagulation. An unbalanced systemic compensatory anti-inflammatory response often results in anergy and immunosuppression.

There remains a need for improved tools to prevent and treat proinflammatory conditions, including proinflammatory skin conditions and epithelial cancers.

SUMMARY OF THE INVENTION

The invention provides HDL-related molecules and methods of using same to treat and prevent proinflammatory conditions and cancer. HDL-related molecules include ApoA-I, bovine HDL, and HDL mimetics. As described in further detail below, ApoA-I, in its natural, full-length form, can prevent UV-induced cell death and oxidative stress. Also described in further detail below is the unexpected discovery that HDL mimetics, ApoA-I and bovine HDL (bHDL) can be used to treat and prevent various cancers.

In one embodiment, the invention provides a method of inhibiting tumor growth. The method comprises contacting tumor cells with an HDL-related molecule selected from the group consisting of HDL mimetic peptides (such as those shown in SEQ ID NO: 1, 3-9, 12, 14 or 26-28), bovine HDL, and ApoA-I. Another embodiment provides a method of treating or preventing cancer in a subject. The method comprises administering to the subject an HDL-related molecule selected from the group consisting of HDL mimetic peptides (such as those shown in SEQ ID NO: 1, 3-9, 12, 14 or 26-28), bovine HDL, and ApoA-I. In yet another embodiment of the invention, a method of reducing death and/or oxidative stress in epithelial cells exposed to oxidative stress is provided. The method comprises contacting the epithelial cells with an HDL-related molecule selected from the group consisting of HDL mimetic peptides (such as those shown in SEQ ID NO: 1, 3-9, 12, 14 or 26-28), bovine HDL, and ApoA-I. In one embodiment, the contacting occurs prior to exposure to oxidative stress. In a typical embodiment, the contacting occurs at least 12-24 hours prior to the exposure to oxidative stress. The oxidative stress may comprise, for example, exposure to ultraviolet radiation.

The HDL-related molecule can, optionally, be administered as an oral supplement. Subjects to be treated with methods of the invention can be, for example, mammalian subjects, typically human subjects.

For use in methods of the invention, the ApoA-I may be full-length protein, which can be administered as recombinant ApoA-I and/or in unmodified form. In one embodiment, the ApoA-I is natural, full-length, unmodified ApoA-I.

The method of any one of claims 1-6, wherein the HDL mimetic peptide is selected from the group consisting of SEQ ID NO: 1, 3-9, 12, 14 and 26-28.

In one embodiment, the invention provides an HDL-related molecule for treatment of cancer, for inhibiting tumor growth, and/or for reducing death and/or oxidative stress in epithelial cells. The HDL-related molecule is selected from the group consisting of HDL mimetic peptides (SEQ ID NO: 1, 3-9, 12, 14 or 26-28), bovine HDL, and ApoA-I. In one embodiment, the invention provides novel HDL mimetic peptides, including those having the amino acid sequences shown in SEQ ID NO: 1, 3-9, 12, 14 or 26-28. In a typical embodiment, the peptide consists of the amino acid sequence shown in SEQ ID NO: 1 or any of those shown in SEQ ID NO: 3-9.

BRIEF DESCRIPTION OF THE FIGURES

FIGS. 4A and 4B show tumor weight and volume, respectively. FIGS. 4C and 4D show the percentage distributions of the scores (control as 100%) of weight and volume, respectively, for each of the three groups. Representative photographs of flank tumors from the three groups are shown in FIG. 4E.

FIGS. 5A and 5B show tumor weight and volume, respectively. FIGS. 5C and 5D show the percentage distributions of the scores (control as 100%) of weight and volume for each of the three groups. Representative photographs of flank tumors from the three groups are shown in FIG. 5E.

FIG. 7A, an apoA-I mimetic peptide, L-4F, inhibits HIF-1α expression and angiogenesis in vivo. Flank tumors were established in wild-type C57BL/6J mice as described in Example 4. Two weeks after tumor growth, mice were treated with scrambled peptide (sc-4F) or L-4F (10 mg/kg s.c., daily injection) for 3 weeks. Frozen sections (5 µm) from dissected tumors were subjected to hematoxylin and eosin (H&E) staining (left), HIF-1α staining (center), and CD31 staining (right). Analysis was done from four randomly selected fields per slide (n=4 mice per group). Representative figures are shown at 400× magnification. Arrows indicate HIF-1α-positive staining. FIG. 7B, pretreatment of L-4F inhibits $CoCl_2$- and insulin-induced HIF-1α expression in human ovarian cancer cell lines. Cells were treated with vehicle or different concentrations of L-4F (1, 3, and 10 µg/ml) for 1 h, and the indicated stimulators were added for another 4 h. Left, pretreatment of L-4F inhibits $CoCl_2$- and insulin-induced HIF-1α expression in OV2008 cells. Right, pretreatment of L-4F inhibits $CoCl_2$- and insulin-induced HIF-1α expression in CAOV-3 cells. FIG. 7C and FIG. 7D, L-4F decreases $CoCl_2$-induced (FIG. 7C) and insulin-induced (FIG. 7D) nuclear expression of HIF-1α in OV2008 cells. Cells were immunostained with a mouse monoclonal anti-HIF-1α primary antibody and a goat anti-mouse IgG labeled with Alexa Fluor 568 (red fluorescence) as the secondary antibody. DAPI was used to stain nuclei (blue in corresponding published manuscript). Images are shown at the original magnification of 200×. Dotted line and boxes show the area where the enlarged images originated. Representative photographs of two independent experiments with similar results are shown. The concentrations of stimulators used were: $CoCl_2$, 100 µM, and insulin, 200 nM.

FIG. 8A, $CoCl_2$-stimulated HRE reporter gene transcription is inhibited by pretreatment of L-4F. OV2008 cells were transfected with pGL3-Epo-HRE-Luc plasmid and grown in complete growth media for 24 h. After an overnight starvation, cells were first treated with L-4F (10 µg/ml) for 1 h and then treated with $CoCl_2$ (100 µM) for an additional 6 h. Luciferase activity was determined as described in Example 4. FIG. 8B, L-4F inhibits expression of HIF-1α target genes in $CoCl_2$-treated cells. After serum starvation overnight, OV2008 cells were treated with L-4F (10 µg/ml) for 1 h and then treated with $CoCl_2$ (100 µM) for an additional 6 h. Total RNA was isolated, and the expression of VEGF, glucose transporter 1 (GLUT1), and aldolase-A (ALDO-A) mRNA levels were measured by real-time RT-PCR. GAPDH was used for normalization. FIG. 8C, insulin-stimulated HRE reporter gene transcription is inhibited by the pretreatment of L-4F. OV2008 cells were transfected with pGL3-Epo-HRE-Luc plasmid and grown in complete growth media for 24 h. After starvation overnight, cells was treated with L-4F (10 µg/ml) for 1 h and then treated with insulin (200 nM) for an additional 16 h. Luciferase activity was determined as described in Example 4. FIG. 8D, L-4F inhibits the expression of HIF-1α target genes in insulin-treated cells. After serum starvation overnight, OV2008 cells were treated with L-4F (10 µg/ml) for 1 h and then treated with insulin (200 nM) for an additional 16 h. Total RNA was isolated and the expression of VEGF, glucose transporter 1 (GLUT1), and aldolase-A (ALDO-A) mRNA levels were measured by real-time RT-PCR. GAPDH was used for normalization. #, $p<0.05$, compared with the corresponding control group. ##, $p<0.01$, compared with the corresponding control group. *, $p<0.05$, compared with the corresponding $CoCl_2$- or insulin-treated groups. **, $p<0.01$, compared with the corresponding $CoCl_2$- or insulin-treated groups. n=3 for each group.

FIGS. 9A-9D. Post-treatment of L-4F decreases HIF-1α protein level and activity in $CoCl_2$- and insulin-treated OV2008 cells. Cells were treated with $CoCl_2$ (100 µM) or insulin (200 nM) for 24 h and then treated with vehicle or L-4F (10 µg/ml) for an additional 1, 2, or 4 h. FIG. 9A, post-treatment of L-4F at 10 µg/ml decreases HIF-1α protein level in $CoCl_2$- and insulin-treated OV2008 cells. FIG. 9B, post-treatment of L-4F at 10 µg/ml for 4 h decreases $CoCl_2$- and insulin-induced increases of nuclear levels of HIF-1α in OV2008 cells. Cells were immunostained with a mouse monoclonal anti-HIF-1α primary antibody and a goat anti-mouse IgG labeled with Alexa Fluor 568 (red fluorescence) as the secondary antibody. DAPI was used to stain nuclei (blue in corresponding published manuscript). Images are shown at the original magnification of 400×. Representative photographs of two independent experiments with similar results are shown. FIG. 9C and FIG. 9D, inhibition of HRE reporter gene transcription in $CoCl_2$- and insulin-treated cells by post-treatment of L-4F. OV2008 cells were transfected with pGL3-Epo-HRE-Luc plasmid and grown in complete growth media for 24 h. After starvation overnight, cells was treated with $CoCl_2$ (100 µM) or insulin (200 nM) for 24 h and then treated with L-4F (10 µg/ml) for an additional 4 h (FIG. 9C) or 24 h (FIG. 9D). Luciferase activity was determined as described in Example 4. **, $p<0.01$, compared with the corresponding $CoCl_2$- or insulin-treated groups. n=3 for each group.

FIGS. 10A-10B. Effect of L-4F on the insulin-stimulated activation of downstream signaling molecules in OV2008 cells. After an overnight starvation, OV2008 cells were treated with L-4F (10 µg/ml) for 1 h, and insulin was added at a final concentration of 200 nM. Cell lysates were collected at various time points and subjected to Western blot analysis. FIG. 10A, L-4F inhibits insulin-stimulated phosphorylation of p70s6 kinase and subsequent HIF-1α expression in OV2008 cells. FIG. 10B, effect of L-4F on insulinstimulated phosphorylation of ERK1/2 and Akt in OV2008 cells.

FIGS. 11A-11B. Effect of L-4F on HIF-1α protein stability in OV2008 cells. FIG. 11A, left, pretreatment of L-4F promotes HIF-1α degradation in OV2008 cells. After an overnight starvation, OV2008 cells were treated with insulin (200 nM) for 3 h, L-4F (10 μg/ml) for 1 h, and CHX (20 μg/ml) for various durations. Cell lysates were collected and subjected to Western blot analysis. Representative data from three independent experiments with similar results are shown. Right, L-4F treatment promotes HIF-1α degradation in OV2008 cells. After an overnight starvation, OV2008 cells were treated with insulin (200 nM) for 3 h and then treated with L-4F (10 μg/ml) and CHX (20 μg/ml) at the same time. Cell lysates were collected at various time points and subjected to Western blot analysis. Representative data from three independent experiments with similar results are shown. FIG. 11B, effect of pretreatment of L-4F on proteasome-mediated degradation of HIF-1α in insulin-treated OV2008 cells. After an overnight starvation, OV2008 cells were treated with MG-132 (10 μM) for 3 h, L-4F (10 μg/ml) for 1 h, and insulin (200 nM) for an additional 4 h. Cell lysates were collected and subjected to Western blot analysis. Representative data from three independent experiments with similar results are shown.

FIG. 12A, L-4F inhibits insulin-stimulated ROS production in OV2008 cells. FIG. 12B, L-4F inhibits $CoCl_2$-stimulated ROS production in OV2008 cells.

FIG. 13A, the data shown are lung weights for mice receiving sc-4F or L-4F administered subcutaneously daily at 10 mg/kg. P<0.01. FIG. 13B, the data shown are the number of tumors counted on the lung surface from the 2 groups of mice. P<0.001. FIG. 13C, representative tumors from the 2 groups of mice showing tumor nodules on the lung surface. FIG. 13D and FIG. 13E, flank tumors were established in BALB/c mice as described in Example 5. Mice were sacrificed 15 days after CT26 cells were administered subcutaneously and tumor weight was measured. FIG. 13D, the data shown are tumor weights for mice receiving sc-4F or L-4F at 10 mg/kg subcutaneously daily. P<0.05. FIG. 13E, representative tumors are shown from 2 groups of mice. w/sc-4F, mice treated with sc-4F; w/L-4F, mice treated with L-4F. F, plasma IL-6 levels from the experiment shown in A. P<0.05.

FIG. 14A, the data shown are lung weights for mice receiving sc-4F (n=12) or L-4F (n=9) mixed into the chow diet at 100 mg/kg/d (2 mg/mouse/d). P<0.05. FIG. 14B, the data shown are the tumor numbers counted on the lung surface from the 2 groups of mice. P<0.0001. FIG. 14C, tumor tissues from the lung surface were sectioned and CD31 immunostaining was done with anti-CD31 antibody for detection of endothelial cells in microvessels. The red stain represents CD31 staining. w/sc-4F, mice treated with sc-4F; w/L-4F, mice treated with L-4F. FIG. 14D, plasma LPA levels were measured as described in Example 5. P<0.01.

FIG. 15A, total tumor numbers in the intestinal tract after treatment with L-4F administered in mouse chow for 8 weeks represented as a percent of the control (i.e., mice treated with sc-4F), P<0.05. FIG. 15B, numbers of tumors in different size categories defined by the diameter of the tumor in mm. w/sc-4F, mice treated with sc-4F; w/L-4F, mice treated with L-4F. FIG. 15C, plasma LPA levels are significantly decreased (>50%) in C57BL/6J-$APC^{min/+}$ mice treated with L-4F compared with control mice. P<0.01.

FIG. 16A, cells were assayed for viability using the MTS assay kit. P<0.001. FIG. 16B, BrdUrd incorporation was analyzed as described in Example 5. P<0.001. FIG. 16C, quantitative analysis of cells in different phases in cell cycle. Data are represented as the mean±SD of the percent of control cells. FIG. 16D, the expression of cyclin D1 and cyclin A. All experiments were conducted in triplicate and each assay was carried out in quadruplicates.

FIG. 17A, CT26 cells were cultured as described in Example 5 and incubated with either L-4F at 10 mg/mL or LPA at a concentration 5, 10, 20 mmol/L, or cells were treated with both L-4F and LPA for 48 hours. All experiments were conducted in triplicate and each assay was carried out in quadruplicates. Data are represented as the mean±SD of the percent of control cells. FIG. 17B, LPA levels were measured in the cell culture medium after 48 hours of treatment.

FIG. 18A, the data shown are lung weights for mice receiving sc-4F (n ¼ 12), G* peptide (n ¼ 12) at 100 mg/kg/d (2 mg/mouse/d) administered in mouse chow. P<0.05. FIG. 18B, the data shown are the tumor numbers on the lung surface from 2 group mice of A. P<0.0001. FIG. 18C, cells were assayed for viability using the MTS assay. P<0.05. D, serum LPA levels from the mice described in FIG. 18A and FIG. 18B were determined as described in Example 5. FIG. 18E, the expression of cyclin D1 and cyclin A by Western blot. w/sc-4F, mice treated with sc-4F; w/G*, mice treated with G* peptide.

DETAILED DESCRIPTION

Figure 1:
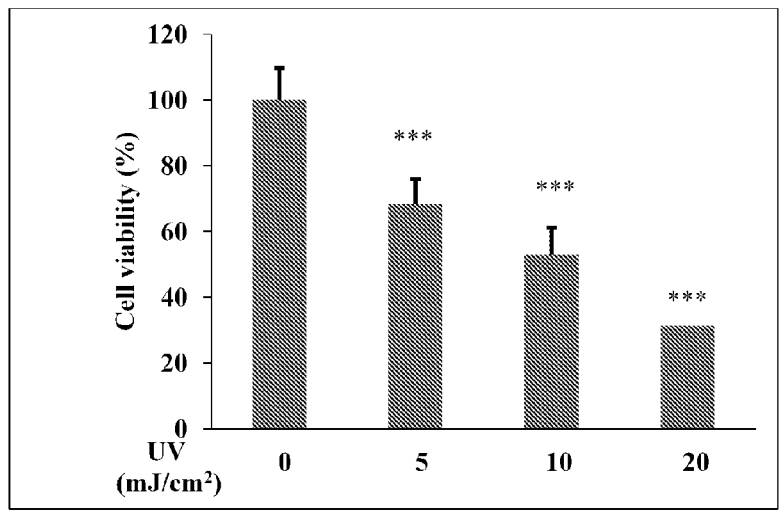
FIG. 1. Bar graph plotting results of assay of cell viability for UV exposed NIH3T3 cells, and showing protective effect of ApoA-l treatment.

The present invention is based on the discovery that HDL-related molecules can be used to treat and prevent proinflammatory conditions. HDL-related molecules include ApoA-I, bovine HDL, and HDL mimetics. As described in further detail below, ApoA-I, in its natural, full-length form, can prevent UV-induced cell death and oxidative stress. Also described in further detail below is the unexpected discovery that HDL mimetics, ApoA-I and bovine HDL (bHDL) can be used to treat and prevent various cancers. ApoA-I and other HDL-related molecules provide potent and effective agents for the treatment and prevention of proinflammatory conditions, including skin conditions, and systemic proinflammatory conditions, including cancer and other diseases, such as Alzheimer's disease. Cancers to be treated include epithelial cancers, such as cancer of the vagina, vulva, ovaries, cervix, uterus, prostate, colon, breast, pancreas, lung, skin (e.g., melanoma), brain (e.g. glioblastoma), and gastric cancer. The HDL-related molecules described herein can also be used in anti-aging treatments, as they can be used to delay the aging process and reduce or eliminate oxidative stress, and in treatment of eye conditions, such as macular degeneration, retinitis pigmentosa, and autoimmune diseases, such as arthritis.

The invention provides a method of reducing death and/or oxidative stress in epithelial cells exposed to oxidative stress. The method comprises contacting the epithelial cells with an HDL-related molecule prior to exposure to oxidative stress. In some embodiments, the oxidative stress comprises exposure to ultraviolet radiation. In a typical embodiment, the contacting occurs at least 12-24 hours prior to the exposure to oxidative stress.

Definitions

All scientific and technical terms used in this application have meanings commonly used in the art unless otherwise specified. As used in this application, the following words or phrases have the meanings specified.

As used herein, "HDL-related molecule" means ApoA-I, bovine HDL, and HDL mimetics, including peptides and synthetic molecules.

As used herein, "ApoA-I" refers to full-length and unmodified ApoA-I, unless context clearly indicates otherwise. For example, "ApoA-I peptides" refers to small portions of full-length ApoA-I. Typically, the ApoA-I is human ApoA-I, a 28.2 kDa protein of 244 amino acids.

As used herein, "HDL mimetics" refers to modified apolipoproteins that mimic the function of HDL, typically providing an HDL-related molecule having enhanced efficacy. Typically, the apolipoproteins are modified by altering or substituting one or more amino acids, and/or by combining two or more HDL peptides to form a chimeric HDL-related molecule.

As used herein, "polypeptide" includes proteins, fragments of proteins, and peptides, whether isolated from natural sources, produced by recombinant techniques or chemically synthesized. Polypeptides of the invention typically comprise at least about 6 amino acids. Shorter polypeptides, e.g., those less than about 50 amino acids in length, are typically referred to as "peptides".

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

The term "nucleic acid" or "polynucleotide" refers to a deoxyribonucleotide or ribonucleotide polymer in either single- or double-stranded form, and unless otherwise limited, encompasses known analogs of natural nucleotides that hybridize to nucleic acids in a manner similar to naturally occurring nucleotides.

As used herein, "pharmaceutically acceptable carrier" or "excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline.

Compositions comprising such carriers are formulated by well known conventional methods (see, for example, *Remington's Pharmaceutical Sciences*, 18th edition, A. Gennaro, ed., Mack Publishing Co., Easton, Pa., 1990).

As used herein, "a" or "an" means at least one, unless clearly indicated otherwise.

HDL Mimetics

The present invention provides HDL mimetics, including chimeras of HDL peptides and modified and/or synthetic molecules that also serve as HDL mimetics. In one embodiment, substitution of alanines in known HDL mimetic peptides with α-aminoisobutyric acid (Aib) generates novel HDL mimetics (NHMs). In a typical embodiment, the chimera comprises two HDL peptides selected from peptides of ApoA-I, ApoE and ApoJ. In one embodiment, the HDL mimetics are obtained via substitution of alanines with α-aminoisobutyric acid (Aib) in an 18 amino acid peptide of Apo A-I that is chimerized with a 10 amino acid peptide of Apo E), to generate NHMs 1-7 described hereinbelow. In another embodiment, the HDL mimetics are obtained via combining ApoE and ApoJ (G*) to generate, for example, the novel HDL mimetic LRKLRKRLLR LVGRQLEEFL (SEQ ID NO: 1).

Substitution of Aib for alanines in E18A (ref) results in a series of seven NHMs.

```
                                          (SEQ ID NO: 2)
E18A peptide (ref) = LRKLRKRLLRDWLKAFYDKVAEKLKEAF NHMs:
                                          (SEQ ID NO: 3)
NHM1 = LRKLRKRLLRDWLKAibFYDKVAEKLKEAF (SEQ ID NO: 4)
NHM2 = LRKLRKRLLRDWLKAFYDKVAibEKLKEAF (SEQ ID NO: 5)
NHM3 = LRKLRKRLLRDWLKAFYDKVAEKLKEAibF (SEQ ID NO: 6)
NHM4 - LRKLRKRLLRDWLKAibFYDKVAibEKLKEAF
```

-continued

NHM5 = LRKLRKRLLRDWLKAFYDKVAibEKLKEAibF (SEQ ID NO: 7)

NHM6 = LRKLRKRLLRDWLKAibFYDKVAEKLKEAibF (SEQ ID NO: 8)

NHM7 = LRKLRKRLLRDWLKAibFYDKVAibEKLKEAibF (SEQ ID NO: 9)

See: Oleg F Sharifov, el al., 2011, Apolipoprotein E Mimetics and Cholesterol Lowering Properties, *American Journal of Cardiovascular Drugs* 11(6):371-381.

Surprisingly, the novel HDL mimetic peptides described herein, alone or in combination with other anti-oxidants, can be used for the prevention and treatment of pro-inflammatory skin and systemic pro-inflammatory conditions, including cancer. These molecules provide potent and effective anti-oxidants for the prevention and treatment of pro-inflammatory skin and systemic pro-inflammatory conditions, including cancer. This has been proved in principle using cell culture models, and has been shown through in vivo studies to inhibit tumor development in an animal model.

Bovine HDL

Bovine HDL (bHDL) as described herein includes the native protein, and heterologous sequences may be present. Typically, the bHDL is used in its natural, full-length, unmodified form. Bovine HDL is typically purified from serum, and can be obtained from, for example, Biomedical Technologies, Inc. (Stoughton, Mass.). Bovine HDL is advantageous relative to the HDL of other species due to its high level of ApoA-I and its high serum levels, as well as its suitability for administration to humans.

ApoA-I Polypeptides

ApoA-I polypeptides as described herein include the native protein, and heterologous sequences may be present. Typically, the ApoA-I is human ApoA-I, used in its natural, full-length, unmodified and mature form.

```
NCBI Reference Sequence: NP_000030.1 (SEQ ID
NO: 10):
    1   mkaavltlav  lfltgsqarh  fwqqdeppqs  pwdrvkdlat
        vyvdvlkdsg  rdyvsqfegs 61   algkqlnlkl  ldnwdsvtst  fsklreqlgp  vtqefwdnle
        keteglrqem  skdleevkak 121   vqpylddfqk  kwqeemelyr  qkveplrael  qegarqklhe
        lqeklsplge  emrdrarahv 181   dalrthlapy  sdelrqrlaa  rlealkengg  arlaeyhaka
        tehlstlsek  akpaledlrq 241   gllpvlesfk  vsflsaleey  tkklntq;
```

In the above sequence, the signal peptide is at amino acids 1-18, the mature proprotein is at amino acids 19-267, and the mature ApoA-I protein is at amino acids 25-267:

(SEQ ID NO: 11)
DEPPQSPWDRVKDLATVYVDVLKDSGRDYVSQFEGSALGKQLNLKLLDNW

DSVTSTFSKLREQLGPVTQEFWDNLEKETEGLRQEMSKDLEEVKAKVQPY

LDDFQKKWQEEMELYRQKVEPLRAELQEGARQKLHELQEKLSPLGEEMRD

RARAHVDALRTHLAPYSDELRQRLAARLEALKENGGARLAEYHAKATEHL

STLSEKAKPALEDLRQGLLPVLESFKVSFLSALEEYTKKLNTQ.

While ApoA-I peptides, and particularly ApoA-I mimetic peptides have been developed in efforts to identify molecules having similar function and/or ease of productive compared to full-length ApoA-I protein for some areas of use, the modifications of these ApoA-I mimetic peptides (e.g., alpha-helical peptides) have rendered them entirely different from natural ApoA-I; in fact, the mimetic peptides share no structural similarity with the full length ApoA-I protein molecule. Moreover, in the area of cardiovascular treatment, the mimetic peptides have been less effective and require such large quantities that therapeutic use of these peptides is impractical. Interestingly, the term mimetic peptide is a term developed over 2 decades ago that refers to an attempt to identify structurally dissimilar molecules that may share some functional properties with the full-length ApoA-I protein; and in fact, no structural similarities exist between these alpha-helical peptides and the full-length ApoA-I molecule. Hence, the term "mimetic peptide" is, in this context, a misnomer, since the ApoA-I full length protein shares nothing structurally in common with its mimetic peptides. The ApoA-I mimetic peptides attempt only to mimic some of the features of the ApoA-I full length protein function.

Variant Polypeptides

A polypeptide of the invention can comprise a variant of a native protein. A polypeptide "variant," as used herein, is a polypeptide that differs from a native protein in one or more substitutions, deletions, additions and/or insertions, such that the therapeutic efficacy of the polypeptide is not substantially diminished. In other words, the efficacy may be enhanced or unchanged, relative to the native protein, or may be diminished by less than 50%, and preferably less than 20%, relative to the native protein. Preferred variants include those in which one or more portions, such as an N-terminal leader sequence, have been removed. Other preferred variants include variants in which a small portion (e.g., 1-30 amino acids, preferably 5-15 amino acids) has been removed from the N- and/or C-terminal of the mature protein. Polypeptide variants preferably exhibit at least about 70%, more preferably at least about 90% and most preferably at least about 95% identity (determined as described above) to the identified polypeptides.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

Preparation of Polypeptides

Polypeptides may comprise a signal (or leader) sequence at the N-terminal end of the protein that co-translationally or post-translationally directs transfer of the protein. The polypeptide may also be conjugated to a linker or other sequence for ease of synthesis, purification or identification of the polypeptide.

Polypeptides may be purified from natural sources, such as serum. In some embodiments, the polypeptides are purified from the same subject to whom the composition will be administered. In other embodiments, the polypeptide is purified from a heterologous species, such as bovine HDL or ApoA-I for administration to humans.

Recombinant polypeptides encoded by DNA sequences as described herein may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, yeast, insect cells or a mammalian cell line such as COS or CHO. Supernatants from suitable host/vector systems that secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Portions and other variants having fewer than about 100 amino acids, and generally fewer than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, J. Am. Chem. Soc. 85:2149-2146, 1963. Equipment for automated synthesis of polypeptides is commercially available from suppliers such as Perkin Elmer/Applied BioSystems Division (Foster City, Calif.), and may be operated according to the manufacturer's instructions.

Polypeptides can be synthesized on a Perkin Elmer/Applied Biosystems Division 430A peptide synthesizer using FMOC chemistry with HPTU (O-BenzotriazoleN,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid: ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%-60% acetonitrile (containing 0.1% TFA) in water may be used to elute the peptides. Following lyophilization of the pure fractions, the peptides may be characterized using electrospray or other types of mass spectrometry and by amino acid analysis.

Fusion Proteins

In some embodiments, the polypeptide is a fusion protein that comprises multiple polypeptides as described herein, or that comprises at least one polypeptide as described herein and an unrelated sequence. In some embodiments, the fusion protein comprises an ApoA-I polypeptide and an immunogenic polypeptide. The immunogenic polypeptide can comprise, for example, all or a portion of an additional protein.

Additional fusion partners can be added. A fusion partner may, for example, serve as an immunological fusion partner by assisting in the provision of T helper epitopes, preferably T helper epitopes recognized by humans. As another example, a fusion partner may serve as an expression enhancer, assisting in expressing the protein at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and the second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., Gene 40:39-46, 1985; Murphy et al., Proc. Natl. Acad. Sci. USA 83:8258-8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located 5' to the DNA sequence encoding the first polypeptides. Similarly, stop codons required to end translation and transcription termination signals are present 3' to the DNA sequence encoding the second polypeptide.

Fusion proteins are also provided that comprise a polypeptide of the present invention together with an unrelated immunogenic protein. Preferably the immunogenic protein is capable of eliciting a memory response. Examples of such proteins include tetanus, tuberculosis and hepatitis proteins (see, for example, Stoute et al., New Engl. J. Med. 336:86-91, 1997).

Within preferred embodiments, an immunological fusion partner is derived from protein D, a surface protein of the gram-negative bacterium *Haemophilus* influenza B (WO 91/18926). Preferably, a protein D derivative comprises approximately the first third of the protein (e.g., the first N-terminal 100-110 amino acids), and a protein D derivative may be lipidated. Other fusion partners include the nonstructural protein from *influenzae* virus, NS I (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; Gene 43:265-292, 1986). LYTA is an autolysin that specifically degrades certain bonds in the peptidoglycan backbone. The C-terminal domain of the LYTA protein is responsible for the affinity to the choline or to some choline analogues such as DEAR This property has been exploited for the development of *E. coli* C-LYTA expressing plasmids useful for expression of fusion proteins. Purification of hybrid proteins containing the C-LYTA fragment at the amino terminus has been described (see Biotechnology 10:795-798, 1992). Within a preferred embodiment, a repeat portion of LYTA may be incorporated into a fusion protein. A repeat portion is found in the C-terminal region starting at residue 178. A particularly preferred repeat portion incorporates residues 188-305.

In general, polypeptides (including fusion proteins) and polynucleotides as described herein are isolated. An "isolated" polypeptide or polynucleotide is one that is removed from its original environment. For example, a naturally occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Polynucleotides of the Invention

The invention provides polynucleotides that encode one or more HDL-related polypeptides, including bHDL, ApoA-I and HDL mimetcs. Polynucleotides that are fully complementary to any such sequences are also encompassed by the present invention. Polynucleotides may be single-stranded (coding or antisense) or double-stranded, and may be DNA (genomic, cDNA or synthetic) or RNA molecules, including siRNA. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials. Portions of such polynucleotides can be useful as primers and probes for the amplification and detection of related molecules.

Polynucleotides may comprise a native sequence (i.e., an endogenous sequence that encodes an HDL-related polypeptide or a portion thereof) or may comprise a variant of such a sequence. Polynucleotide variants contain one or more substitutions, additions, deletions and/or insertions such that the immunogenicity of the encoded polypeptide is not diminished, relative to a native protein. Variants preferably exhibit at least about 70% identity, more preferably at least about 80% identity and most preferably at least about 90% identity to a polynucleotide sequence that encodes a native protein or a portion thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 Methods in Enzymology vol. 183, Academic Press, Inc., San Diego, Calif.; Higgins, D. G. and Sharp, P. M. (1989) CABIOS 5:151-153; Myers, E. W. and Muller W. (1988) CABIOS 4:11-17; Robinson, E. D. (1971) Comb. Theor. 11:105; Santou, N., Nes, M. (1987) Mol. Biol. Evol. 4:406-425; Sneath, P. H. A. and Sokal, R. R. (1973) Numerical Taxonomy the Principles and Practice of Numerical Taxonomy, Freeman Press, San Francisco, Calif.; Wilbur, W. J. and Lipman, D. J. (1983) Proc. Natl. Acad. Sci. USA 80:726-730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native protein (or a complementary sequence).

Suitable "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Polynucleotides may be prepared using any of a variety of techniques known in the art. DNA encoding an ApoA-I protein may be obtained from a cDNA library prepared from tissue expressing the corresponding mRNA. Accordingly, human ApoA-I DNA can be conveniently obtained from a cDNA library prepared from human tissue. The ApoA-I protein-encoding gene may also be obtained from a genomic library or by oligonucleotide synthesis. Libraries can be screened with probes (such as antibodies to ApoA-I or oligonucleotides of at least about 20-80 bases) designed to identify the gene of interest or the protein encoded by it. Screening the cDNA or genomic library with the selected probe may be conducted using standard procedures, such as those described in Sambrook et al., *Molecular Cloning: A Laboratory Manual* (New York: Cold Spring Harbor Laboratory Press, 1989). An alternative means to isolate the gene encoding ApoA-I is to use PCR methodology (Sambrook et al., supra; Dieffenbach et al., *PCR Primer: A Laboratory Manual* (Cold Spring Harbor Laboratory Press, 1995)).

The oligonucleotide sequences selected as probes should be sufficiently long and sufficiently unambiguous that false positives are minimized. The oligonucleotide is preferably labeled such that it can be detected upon hybridization to DNA in the library being screened. Methods of labeling are well known in the art, and include the use of radiolabels, such as $^{32}$P-labeled ATP, biotinylation or enzyme labeling. Hybridization conditions, including moderate stringency and high stringency, are provided in Sambrook et al., supra.

Polynucleotide variants may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis (see Adelman et al., DNA 2:183, 1983). Alternatively, RNA molecules may be generated by in vitro or in vivo transcription of DNA sequences encoding an ApoA-I protein, or portion thereof, provided that the DNA is incorporated into a vector with a suitable RNA polymerase promoter (such as T7 or SP6). Certain portions may be used to prepare an encoded polypeptide, as described herein. In addition, or alternatively, a portion may be administered to a patient such that the encoded polypeptide is generated in vivo.

Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine.

Nucleotide sequences can be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Within certain embodiments, polynucleotides may be formulated so as to permit entry into a cell of a mammal, and to permit expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art.

Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Pharmaceutical Compositions

The invention provides ApoA-I polypeptide, polynucleotides, and related molecules that are incorporated into pharmaceutical compositions. In a typical embodiment, the polypeptide is ApoAI in natural, full-length, unmodified form. As is understood in the art, ApoAI is a significant component of high-density lipoprotein (HDL). Accordingly, one can administer ApoAI by administering HDL.

Pharmaceutical compositions comprise one or more such compounds and, optionally, a physiologically acceptable carrier. Administration of ApoAI is facilitated by preparation with inert lipids, e.g. to form micelles. In a typical embodiment, ApoAI is administered orally, as part of an oral supplement. Alternatively, it can be administered transdermally, such as via a patch adhered to the subject's skin.

While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous, intradermal, transdermal or intramuscular administration. For parenteral administration, such as subcutaneous injection, the carrier preferably comprises a fat, and optionally water, saline, alcohol, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention.

In addition, the carrier may contain other pharmacologically-acceptable excipients for modifying or maintaining the pH, osmolarity, viscosity, clarity, color, sterility, stability, rate of dissolution, or odor of the formulation. Similarly, the carrier may contain still other pharmacologically-acceptable excipients for modifying or maintaining the stability, rate of dissolution, release, or absorption or penetration across the blood-brain barrier of the molecule. Such excipients are those substances usually and customarily employed to formulate dosages for parenteral administration in either unit dose or multi-dose form or for direct infusion into the CSF by continuous or periodic infusion from an implanted pump.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate. Compounds may also be encapsulated within liposomes using well known technology.

A pharmaceutical composition can contain DNA encoding one or more of the polypeptides as described above, such that the polypeptide is generated in situ. As noted above, the DNA may be present within any of a variety of delivery systems known to those of ordinary skill in the art, including nucleic acid expression systems, bacteria and viral expression systems. Numerous gene delivery techniques are well known in the art, such as those described by Rolland, Crit. Rev. Therap. Drug Carrier Systems 15:143-198, 1998, and references cited therein. Appropriate nucleic acid expression systems contain the necessary DNA sequences for expression in the patient (such as a suitable promoter and terminating signal). Bacterial delivery systems involve the administration of a bacterium (such as *Bacillus-Calmette-Guerrin*) that expresses an immunogenic portion of the polypeptide on its cell surface or secretes such an epitope.

In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., Proc. Natl. Acad. Sci. USA 86:317-321, 1989; Flexner et al., Ann. N. Y. Acad Sci. 569:86-103, 1989; Flexner et al., Vaccine 8:17-21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner-Biotechniques 6:616-627, 1988; Rosenfeld et al., Science 252:431-434, 1991; Kolls et al., Proc. Natl. Acad. Sci. USA 91:215-219, 1994; Kass-Eisler et al., Proc. Natl. Acad. Sci. USA 90:11498-11502, 1993; Guzman et al., Circulation 88:2838-2848, 1993; and Guzman et al., Cir. Res. 73:1202-1207, 1993. Techniques for incorporating DNA into such expression systems are well known to those of ordinary skill in the art. The DNA may also be "naked," as described, for example, in Ulmer et al., Science 259:1745-1749, 1993 and reviewed by Cohen, Science 259:1691-1692, 1993. The uptake of naked DNA may be increased by coating the DNA onto biodegradable beads, which are efficiently transported into the cells.

Any of a variety of adjuvants may be employed in the compositions of this invention. Most adjuvants contain a substance designed to protect the peptide from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); aluminum salts such as aluminum hydroxide gel (alum) or aluminum phosphate; salts of calcium, iron or zinc; an insoluble suspension of acylated tyrosine acylated sugars; cationically or anionically derivatized polysaccharides; polyphosphazenes biodegradable microspheres; monophosphoryl lipid A and quil A. Cytokines, such as GM CSF or interleukin-2, -7, or -12, may also be used as adjuvants.

The compositions described herein may be administered as part of a sustained release formulation (i.e., a formulation such as a capsule or sponge that effects a slow release of compound following administration). Such formulations may generally be prepared using well known technology and administered by, for example, oral, rectal or subcutaneous implantation, or by implantation at the desired target site, such as a site of surgical excision of a tumor. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

Administration and Dosage

The compositions are administered in any suitable manner, often with pharmaceutically acceptable carriers or in the form of a pharmaceutically acceptable salt. Suitable methods of administering ApoA-I in the context of the present invention to a subject are available, and, although more than one route can be used to administer a particular composition, a particular route can often provide a more immediate and more effective reaction than another route.

The dose administered to a patient, in the context of the present invention, should be sufficient to effect a beneficial therapeutic response in the patient over time, or to inhibit disease progression. Thus, the composition is administered to a subject in an amount sufficient to elicit an effective to alleviate, reduce, cure or at least partially arrest symptoms and/or complications from the disease.

An amount adequate to accomplish this is defined as a "therapeutically effective dose." In general, for pharmaceutical compositions comprising one or more polypeptides, the amount of each polypeptide present in a dose ranges from about 100 µg to 5 mg per kg of host. Suitable volumes will vary with the size of the patient, but will typically range from about 0.1 mL to about 5 mL.

Routes and frequency of administration of the therapeutic compositions disclosed herein, as well as dosage, will vary from individual to individual, and may be readily established using standard techniques. In general, the pharmaceutical compositions may be administered, by injection (e.g., intracutaneous, intratumoral, intramuscular, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. In one embodiment, 2 or more oral supplements are administered 10 days apart.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients.

Treatment includes prophylaxis and therapy. Prophylaxis or therapy can be accomplished by a single administration at a single time point or multiple time points to a single or multiple sites. Administration can also be nearly simultaneous to multiple sites. Patients or subjects include mammals, such as human, bovine, equine, canine, feline, porcine, and ovine animals. The subject is preferably a human. In a typical embodiment, treatment comprises administering to a subject ApoAI in its natural, unmodified, full-length form.

EXAMPLES

The following examples are presented to illustrate the present invention and to assist one of ordinary skill in making and using the same. The examples are not intended in any way to otherwise limit the scope of the invention.

Example 1

ApoA-1 Prevents UV-Induced Cell Death and Oxidative Stress in NIH-3T3 Fibroblasts This example demonstrates that ApoA-1 treatment prevents UV-induced cell death and oxidative stress in NIH-3T3 fibroblasts (skin cells). NIH 3T3 ($1 \times 10^6$) ells were seeded in 96 well plates in 4 separate plates. After 24 hrs, cells were starved overnight. Apo A-1 was used at a concentration (10 µg/ml) to treat the cells for 24 hrs. After treatment of cells were washed with PBS. One plate was used as a control without UV treatment. The remaining three plates were used for UV treatment at 5, 10, and 20 mJ/cm$^2$. Following UV treatment, cells were given complete media and were cultured for another 24 hrs. Cell viability was measured for all the plates as described previously (Ganapathy E, et al., 2011, D-4F, an apoA-1 mimetic peptide inhibits proliferation and tumorigenicity of epithelial ovarian cancer cells by upregulating the antioxidant enzyme MnSOD, *Int J Cancer* 130: 1071-1081).

Figure 2:
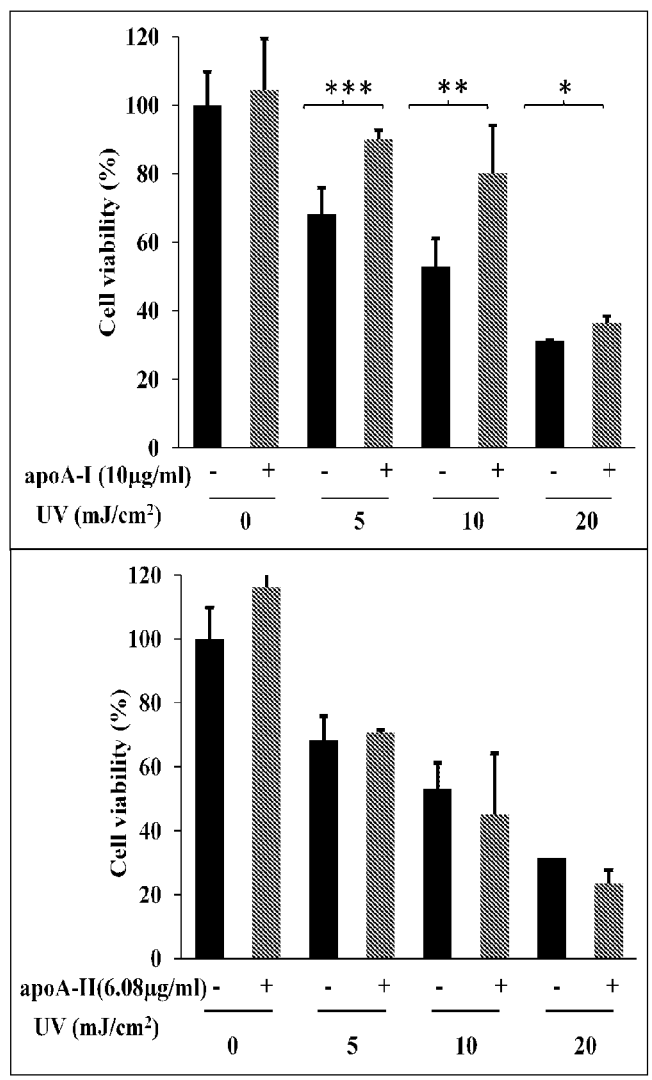
FIG. 2. Bar graphs plotting cell viability and showing that ApoA-l (upper panel) pre-treatment (10 μg/ml) protects NIH3T3 cells from UV-induced cell death, while ApoA-II (lower panel), a protein that is also associated with HDL like apoA-I, did not prevent UV-induced cell death of NIH3T3 cells.

Results showed that UV treatment reduces cell viability in NIH3T3 cells (FIG. 1). ApoA-1 treatment (10 µg/ml) protects NIH3T3 cells from UV-induced cell death (FIG. 2). ApoA-II, a protein that is also associated with HDL like apoA-I, did not prevent UV-induced cell death of NIH3T3 cells (FIG. 2). Thus, ApoA-1 effectively prevents UV-induced cell death and oxidative stress in NIH-3T3 fibroblasts (skin cells). ApoA-I has a potential role in the prevention and treatment of pro-inflammatory skin conditions.

Example 2

Inhibition of Tumor Growth and Development Using Bovine HDL

This example demonstrates that bHDL (bovine HDL) affects pro-inflammatory conditions, such as tumor growth and development, in mouse models of colon cancer. bHDL reduced viability and proliferation of CT26 cells, a mouse colon adenocarcinoma cell line and decreased CT26 cell-mediated tumor burden in BALB/c mice when administered subcutaneously or orally. Plasma levels of lysophosphatidic acid (LPA), a serum biomarker for colon cancer, were significantly reduced in mice that received bHDL mimetics as well, suggesting that binding and removal of pro-inflammatory lipids is a potential mechanism for the inhibition of tumor development by bHDL. Furthermore, bHDL significantly reduced size and number of polyps in APC$^{min/+}$ mice, a mouse model for human familial adenomatous polyposis.

Recent studies suggest that HDL levels are inversely related to colon cancer risk. HDL mimetics constructed from a number of peptides and proteins with varying structures possess anti-inflammatory and antioxidant properties reminiscent of HDL. The results presented in this example show that bHDL molecules are effective in inhibiting the development of both induced and spontaneous pro-inflammatory conditions, such as cancers of the colon. These results, for the first time, identify bHDL as a novel therapeutic strategy for the treatment of pro-inflammatory conditions, here exemplified by the prevention and treatment of colon cancer.

Mice

The Animal Research Committee at the University of California at Los Angeles approved all mouse protocols. 6-week-old BALB/c female mice and 6-week-old C57BL/6J-APC$^{Min/+}$ male mice were purchased from The Jackson Laboratory.

bHDL bHDL were obtained from Biomedical Technologies Inc. For administration of bHDL in the diet, the bHDL was mixed into standard mouse chow (Ralston Purina) using techniques essentially as described previously for a Western diet (18). However, the Western diet was not administered in any of the experiments reported here; the mice only received standard mouse chow with or without the bHDL.

Cell-Culture Experiments

CT26 cell line derived from N-nitroso-N-methyl urethane-induced mouse colon carcinoma of BALB/c origin was purchased from the American Type Culture Collection (ATCC). CT26 cells (2,000 cells per well) were first cultured in complete medium in 96-well culture plates, and 24 hours later the medium was replaced with serum free medium. Following an overnight incubation, the cells were either treated with vehicle (control), or treated with 10 µg/mL of either bHDL. The bHDL were dissolved in H2O. Cells were incubated for an additional 48 hours and assayed for viability using the MTS assays kit (Promega) according to the manufacturer's protocol. For proliferation assay, cells were labeled with BrdU for the last 4 hours of the 48 hours incubation. Cells were subsequently washed, fixed, and incubated with mouse anti-BrdU antibody for 1 hour at room temperature and detected by a peroxidase-coupled goat anti-mouse secondary antibody (Calbiochem). Absorbance was measured using dual wavelengths 450 and 540 nm.

Tumor-Load Study 6-week-old BALB/c female mice were given a 100 μL subcutaneous injection of 1×10⁶ CT26 cells prepared as a single cell suspension in PBS, and the mice were treated with bHDLor BHDLat 10 mg/kg administered subcutaneously (SQ) daily for 15 days. The mice were sacrificed and tumor weights were measured.

Pulmonary Metastasis In Vivo.

BALB/c mice were intravenously injected with 2×10⁴ CT26 cells in 100 μL of PBS via tail vein injection and the mice were treated with bHDL at 10 mg/kg/day administered SQ for 3 weeks; or treated with bHDL at 100 mg/kg/day administered in a chow diet for 3 weeks. After 3 weeks treatment, the mice were sacrificed; lungs were harvested, weighed and fixed with Bouin's solution (Sigma). Tumor nodules on the lung surface were counted.

$APC^{Min/+}$ Mice Study 6-week-old $APC^{Min/+}$ male mice on a C57BL/6J background were treated with bHDL 100 mg/kg/day administered in a chow diet. After 8 weeks treatment, mice were sacrificed. The entire intestine was immediately removed, fixed in formalin and 70% ethanol. The intestine was opened and examined under a dissecting microscope to count and measure the tumors.

Immunohistochemistry (IHC) Staining

Tumor tissues from the lung surface were fixed and embedded with paraffin, sectioned at 5 μm thickness. Sections were deparaffinized with xylene, rehydrated with 100%, 90%, 70%, and 50% ethanol, treated with proteinase K at 20 μg/mL for 30 min, and treated with 3% $H_2O_2$ for 30 min at room temperature to inhibit endogenous peroxidase, blocked with 10% normal goat serum and 4% BSA prepared in PBS for 3 h, and then incubated with 1:50 rat anti-mouse monoclonal CD31 antibody overnight at 4° C. The sections were incubated with corresponding biotinylated secondary antibody for 1 hour, followed by incubation with Vectastain ABC Elite reagents.

Cell Cycle Analysis

CT26 cells were cultured in 6-well plates overnight and then serum starved for 48 hours. Cells were either treated with vehicle (control), or treated with 10 μg/mL of BHDLor G* bHDL, and incubated for an additional 48 hours. Cells were collected, washed with PBS, and fixed with 70% ice-cold methanol overnight at 4° C. The fixed cells were collected by centrifugation, washed with PBS, and resuspended in 0.3 ml of PBS containing 40 μg/mL RNaseA and 100 μg/mL Propidium Iodide, and subjected to flow cytometric cell-cycle analysis by FACScan from BD Biosciences.

Western Blot Analysis

Total cell proteins were collected after treatment in cell lysis buffer containing 0.1M NaCl, 5 mM EDTA, 50 mM sodium orthovanadate, 1% Triton X-100, and protease inhibitor tablet in 50 mM Tris buffer (pH 7.5). 20 g of total proteins were separated by SDS-PAGE and transferred onto nitrocellulose membrane, and followed by incubation with primary antibody at 4° C. in 5% skim milk and 0.1% Tween-20. Anti-Cyclin D1 and anti-Cyclin A rabbit polyclonal antibodies were used at 1:1000 dilution, and anti-β-actin molyclonal antibody was used at 1:2000 dilution.

ELISA Analysis

Il-6 concentrations were measured in plasma by a competition ELISA according to the manufacture's protocol (Invitrogen).

LPA Binding Affinity and Serum LPA Levels

LPA (20:4) was purchased from Avanti Polar Lipids. LPA levels were determined as described previously (Murph et al., 2007, Methods Enymol 433:1-25).

Statistical Analyses

The data are shown as means±SD for each group. We performed statistical analyses by unpaired t test. All results were considered statistically significant at $P<0.05$.

Results

Figure 3:
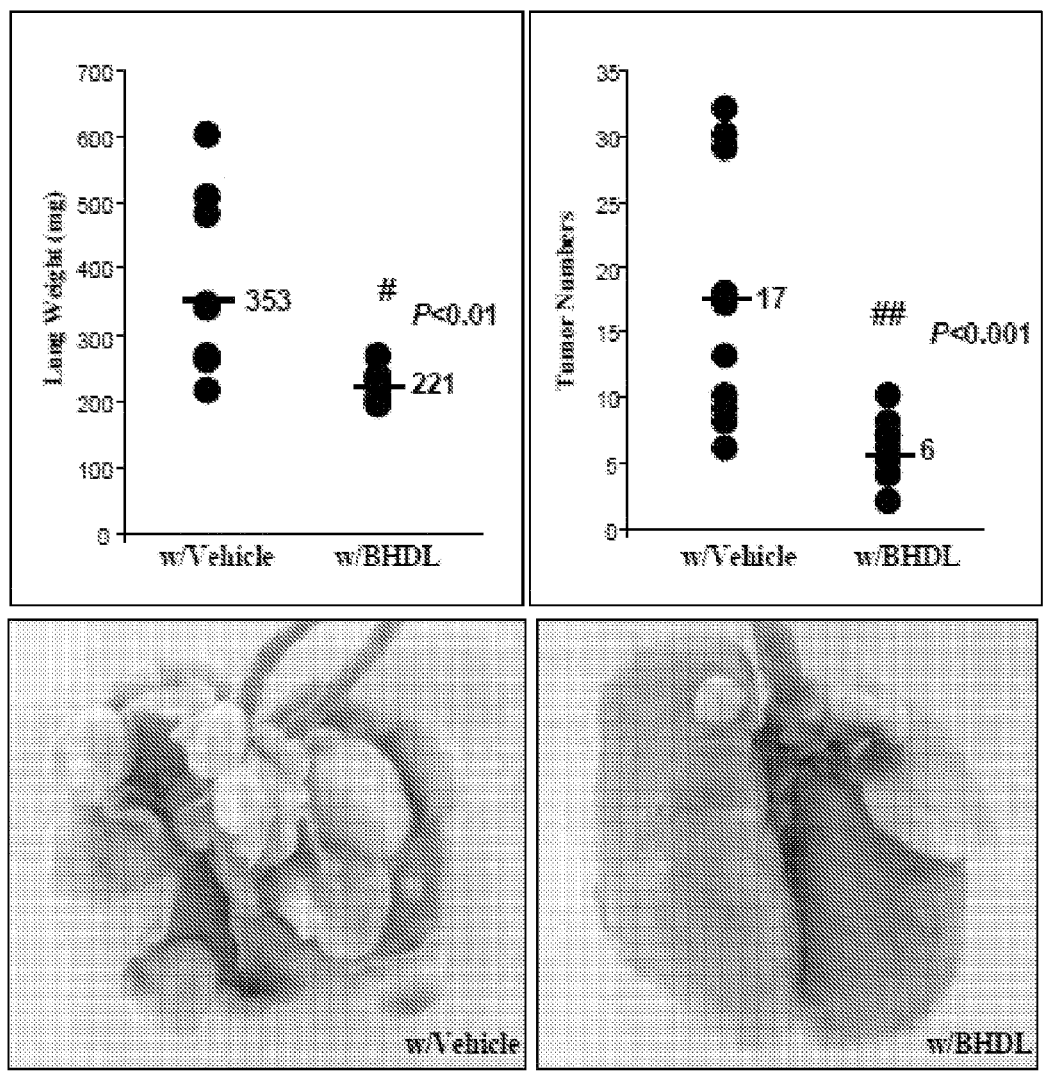
FIG. 3. Graphic and digital photomicrographic depiction of lung weight and tumor volume, comparing treatment with bHDL and vehicle control in $APC^{min/+}$ mice, a mouse model for human familial adenomatous polyposis.

The results are shown in FIG. 3. Evaluation of both lung weight and tumor volume, as well as visual inspection, showed that bHDL significantly reduced size and number of polyps in $APC^{min/+}$ mice, a mouse model for human familial adenomatous polyposis.

Example 3

Inhibition of Tumor Development Using HDL Mimetics

This example demonstrates that HDL mimetics can be used to inhibit tumor development in a mouse model of colon cancer.

Mice

The Animal Research Committee at the University of California at Los Angeles approved all mouse protocols. 6-week-old BALB/c female mice were purchased from The Jackson Laboratory.

Peptides

An apoA-I mimetic peptide L-4F (Ac-D-W-F-K-A-F-Y-D-K-V-A-E-K-F-K-E-A-F-$NH_2$; SEQ ID NO: 12) and a scrambled peptide (sc-4F) containing the same amino acids as in the 4F peptides but arranged in a sequence (Ac-D-W-F-A-K-D-Y-F-K-K-A-F-V-E-E-F-A-K-$NH_2$; SEQ ID NO: 13) that prevents the formation of a class A amphipathic helix were all synthesized from all L-amino acids. Also tested was another peptide, named L-4F2 (Ac-D-W-F-K-A-F-Y-D-K-V-Aib-E-K-F-K-E-Aib-F-$NH_2$; SEQ ID NO: 14), in which $A^{11}$ and $A^{17}$ were substituted with α-aminoisobutyric acid (Aib). Peptide Ac-hE18A-$NH_2$ (28AA) has the amino acid sequence L-R-K-L-R-K-R-L-L-R-D-W-L-K-A-F-Y-D-K-V-A-E-K-L-K-E-A-F (SEQ ID NO: 2), which has the dual domain, derived by covalently linking the heparin binding domain 141-150 (L-R-K-L-R-K-R-A-L-L-R; SEQ ID NO: 15) of apoE to 8A, a class A amphipathic helical peptide. Peptide 28AA-2 with sequence L-R-K-L-R-K-R-L-L-R-D-W-L-K-A-F-Y-D-K-V-Aib-E-K-L-K-E-Aib-F (SEQ TD NO: 7) in which $A^{11}$ and $A^{17}$ were substituted with α-aminoisobutyric acid (Aib). All the peptides were dissolved in $H_2O$.

Cell-Culture Experiments

CT26 and NIH3T3 cells (2,000 cells per well) were first cultured in complete medium in 96-well culture plates, and 24 hours later the medium was replaced with serum-free medium. Following an overnight incubation, the cells were either treated with vehicle (control), or treated with 10 μg/mL of either L-4F or L-4F2 or 28AA or 28AA-2 peptide. Cells were incubated for an additional 48 hours and assayed for viability using MTS assays kit (Promega) according to the manufacturer's protocol.

Tumor-Load Study 6-week-old BALB/c female mice were given a 100 μl subcutaneous injection of 1×10⁶ CT26 cells prepared as a single cell suspension in PBS, treated with peptide at 10 mg/kg by SQ daily for 15 days.

The mice were killed and tumor weights were measured. The tumor volumes were measured using the formula $V=½(L×W^2)$.

LPA Binding Affinity and Serum LPA Levels

LPA (20:4) was purchased from Avanti Polar Lipids. Serum LPA levels were determined as described previously (18).

Statistical Analyses

The data are shown as means±SD for each group. We performed statistical analyses by unpaired t test. All results were considered statistically significant at P<0.05.

the Peptides Inhibit Tumor Development Following CT26 Cell Injection in BALB/c Mice.

Figure 4:
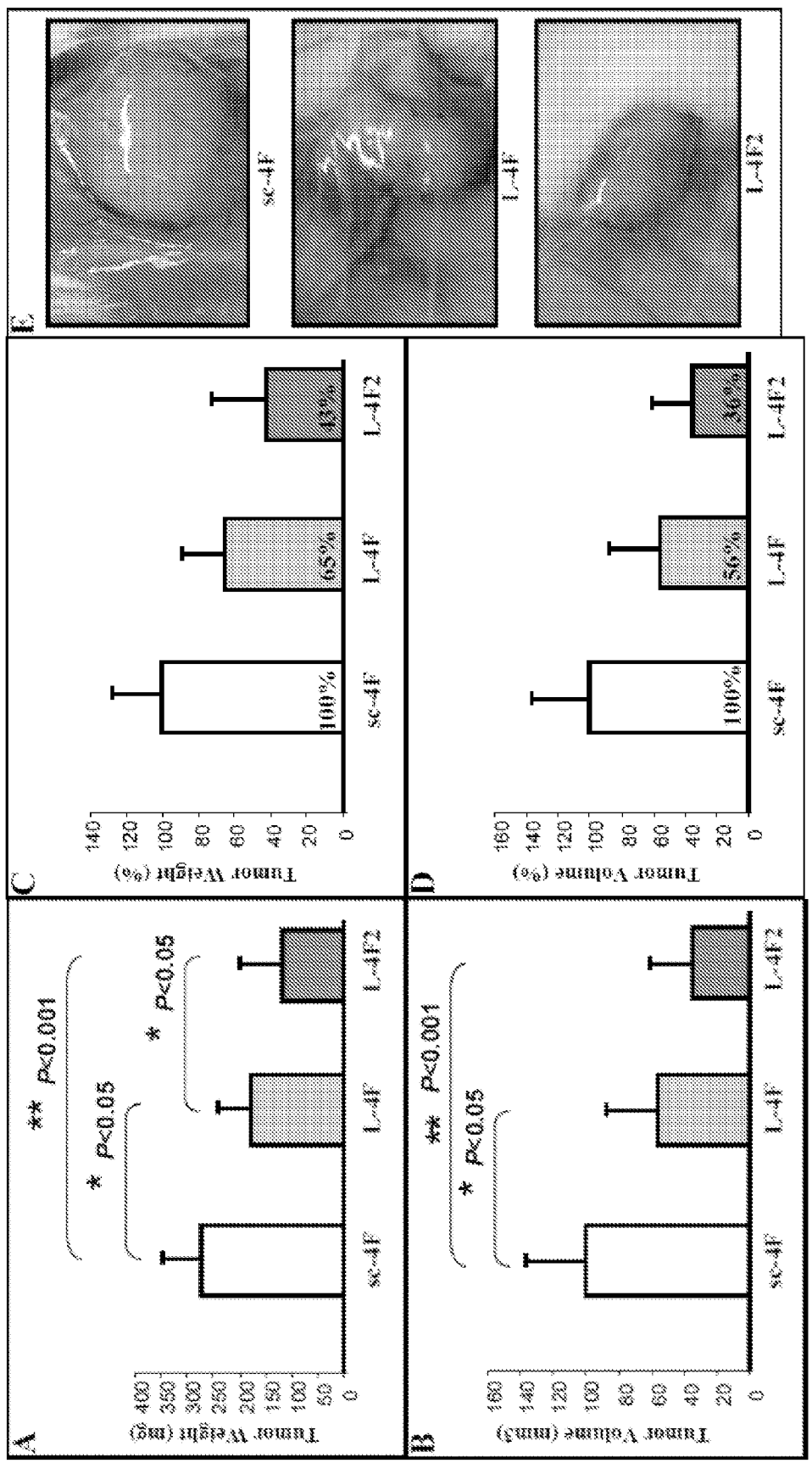
FIGS. 4A-4E. Graphic and digital photomicrographic depiction of effects on flank tumor weights and volumes in BALB/c mice treated with sc-4F compared with mice treated with L-4F and L-4F2.

CT-26 is a colon adenocarcinoma cell line which develops metastatic pulmonary tumors when introduced intravenously into immunocompetent BALB/c mice. We first examined the effect of L-4F, L-4F2 and sc-4F (a scrambled peptide containing the same amino acids as in the 4F peptide but arranged in a sequence that prevents the formation of a class A amphipathic helix) administered by SQ at 10 mg/kg/day on flank tumor formation in BALB/c mice injected with $1 \times 10^6$ CT26 cells subcutaneously in the flank. The mice were treated with either sc-4F (n=9) or L-4F (n=8) or L-4F2 (n=10) at 10 mg/kg by subcutaneous injection daily for 15 days at a site distant from the site where the CT26 cells were injected. The flank tumor weights and volumes were significantly larger in BALB/c mice treated with sc-4F compared with mice treated with L-4F, as expected (273 mg vs. 179 mg, P<0.05; 555 mm$^3$ vs. 313 mm$^3$, P<0.05. FIG. 4A,4B); and also the tumor weights and volumes were significantly larger in mice treated with sc-4F compared with mice treated with L-4F2 (273 mg vs. 118 mg, P<0.001; 555 mm$^3$ vs. 197 mm$^3$, P<0.001. FIG. 4A,4B). The tumors from the mice treated with L-4F2 were significantly smaller compared with mice treated with L-4F (179 mg vs. 118 mg, P<0.05; 313 mm$^3$ vs. 197 mm$^3$. FIG. 4A,4B). Representative photographs of flank tumors from the three groups are shown in FIG. 4E. FIGS. 4C and 4D show the percentage distributions of the scores (control as 100%) of weight and volume for each of the three groups.

Figure 5:
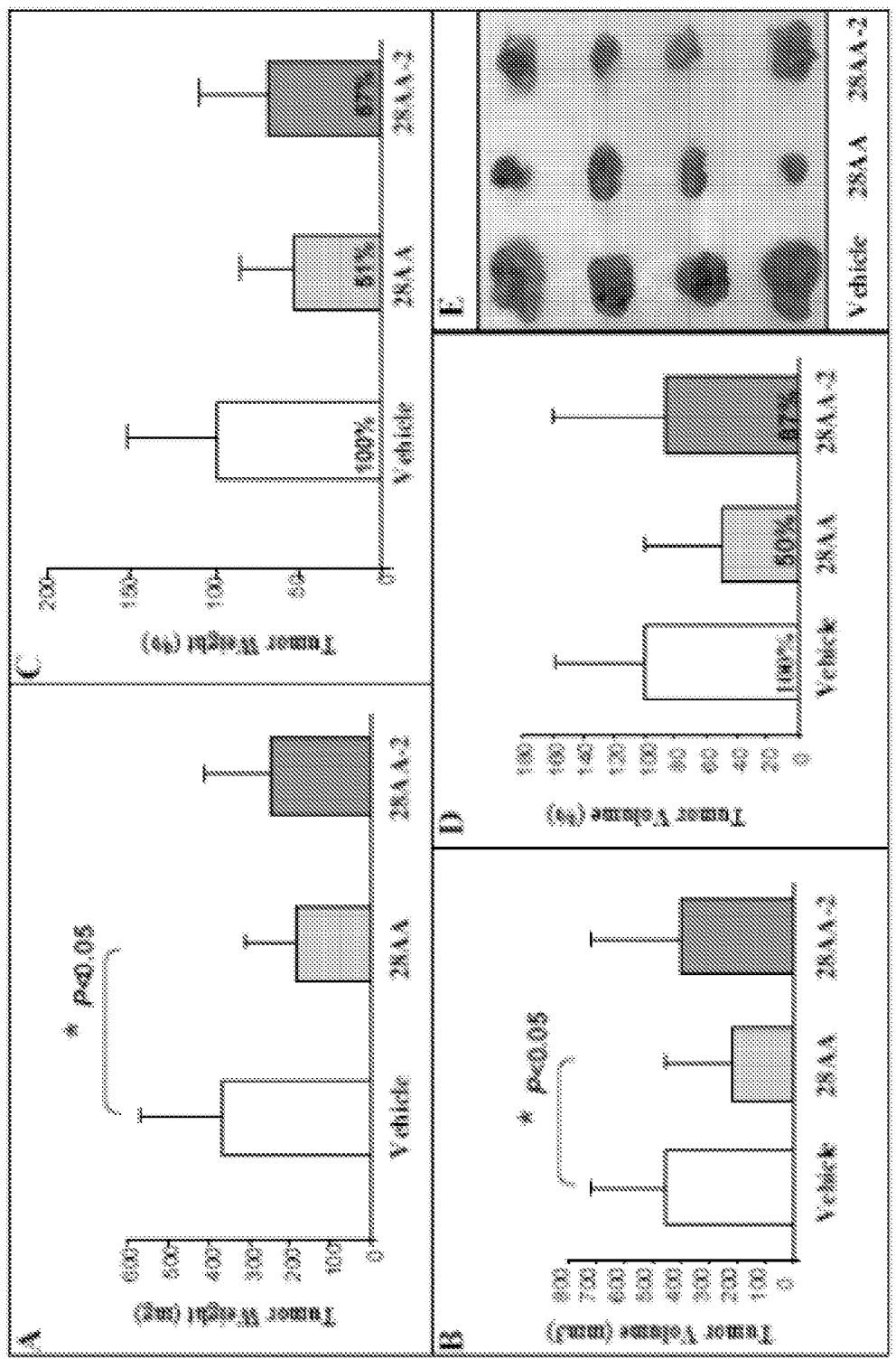
FIGS. 5A-5E. Graphic and digital photomicrographic depiction of effects on flank tumor weights and volumes in BALB/c mice treated with 28AA and 28AA-2 peptide that had been injected with CT26 cells subcutaneously in the flank. The mice were treated with either vehicle (n=12) or 28AA (n=10) or 28AA-2 (n=11) at 10 mg/kg by subcutaneous injection daily for 15 days at a site distant from the site where the CT26 cells were injected.

We next examined whether 28AA and 28AA-2 peptide treatment affects the development of tumors in the flanks of BALB/c mice. 6-week-old BALB/c female mice were injected with $1 \times 10^6$ CT26 cells subcutaneously in the flank. The mice were treated with either vehicle (n=12) or 28AA (n=10) or 28AA-2 (n=1) at 10 mg/kg by subcutaneous injection daily for 15 days at a site distant from the site where the CT26 cells were injected. The flank tumor size and weight were significantly larger in BALB/c mice treated with vehicle compared with mice treated with 28AA (371 mg vs. 188 mg, P<0.05) (FIG. 5A, 5B). FIGS. 5C and 5D show the percentage distributions of the scores (control as 100%) of weight and volume for each of the three groups. Representative photographs of flank tumors from the three groups are shown in FIG. 5E.

The Peptides Inhibit CT26 Cell Viability, but not NIH3T3 Cells In Vitro.

Figure 6:
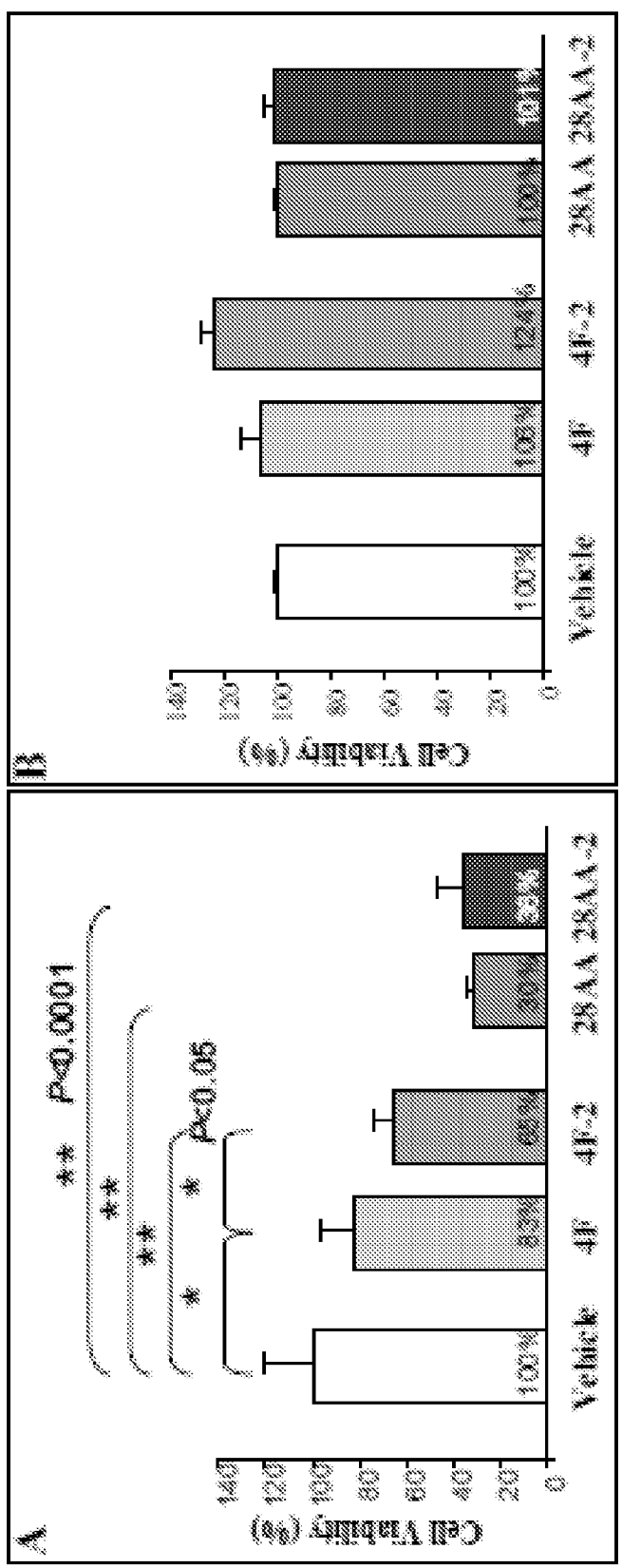
FIGS. 6A and 6B plot results of an MTS cell viability assay. CT26 cells were treated with L-4F, L-4F2, 28AA or 28AA-2 peptides (10 µg/ml) and compared with control (FIG. 6A). NIH3T3 cell viability was also determined in vitro with the treatment with all of 4 peptides. NIH3T3 cell viability was not affected by any of the 4 peptides (FIG. 6B).

To examine the mechanisms by which the peptides inhibit CT26 cell-mediated tumor development in mice, the effect of the peptides on CT26 cell viability was determined in vitro. Cell viability was reduced by more than 20% (P<0.05) in CT26 cells that were treated with L-4F (10 µg/ml) when compared with control (FIG. 6A), and also cell viability was reduced more than 30% (P<0.0001) in CT26 cells that were treated with L-4F2 (10 g/ml) compared with control (FIG. 6A). Moreover, CT26 cell viability was significantly reduced (P<0.05) with the treatment with L-4F2 compared with L-4F treatment (FIG. 6A). CT26 cell viability was determined in vitro with the treatment with 28AA and 28AA-2 peptide. Cell viability was reduced by 70% (P<0.0001) in CT26 cells that were treated with 28AA peptide (10 µg/ml) and reduced by 64% (P<0.0001) in cells that were treated with 28AA-2 (10 µg/ml), when compared with control (FIG. 6A). NIH3T3 cell viability was also determined in vitro with the treatment with all of 4 peptides. NIH3T3 cell viability was not affected by any of 4 peptides (FIG. 6B).

Example 4

Apolipoprotein A-I Mimetic Peptides Inhibit Expression and Activity of Hypoxia-Inducible Factor-1 in Human Ovarian Cancer Cell Lines and a Mouse Ovarian Cancer Model This example demonstrates that apoA-I mimetic peptides inhibit the expression and activity of hypoxia-inducible factor-1α (HIF-1α), which plays a critical role in the production of angiogenic factors and angiogenesis. Immunohistochemistry staining was used to examine the expression of HIF-1α in tumor tissues. Immunoblotting, real-time polymerase chain reaction, immunofluorescence, and luciferase activity assays were used to determine the expression and activity of HIF-1α in human ovarian cancer cell lines. Immunohistochemistry staining demonstrated that L-4F treatment dramatically decreased HIF-1α expression in mouse ovarian tumor tissues. L-4F inhibited the expression and activity of HIF-1α induced by low oxygen concentration, cobalt chloride ($CoCl_2$, a hypoxiamimic compound), lysophosphatidic acid, and insulin in two human ovarian cancer cell lines, OV2008 and CAOV-3. L-4F had no effect on the insulin-induced phosphorylation of Akt, but inhibited the activation of extracellular signal-regulated kinase and p70s6 kinase, leading to the inhibition of HIF-1α synthesis. Pretreatment with L-4F dramatically accelerated the proteasome-dependent protein degradation of HIF-1α in both insulin and $CoCl_2$-treated cells. The inhibitory effect of L-4F on HIF-1α expression is in part mediated by the reactive oxygen species scavenging effect of L-4F. ApoA-I mimetic peptides inhibit the expression and activity of HIF-1α in both in vivo and in vitro models, suggesting the inhibition of HIF-1α may be a critical mechanism responsible for the suppression of tumor progression by apoA-I mimetic peptides.

Tumor angiogenesis plays a critical role in the growth and progression of solid tumors, including ovarian cancer (Folkman, 1971; Hanahan and Folkman, 1996; Carmeliet and Jain, 2000; note that complete citations to REFERENCES throughout Example 4 can be found in Gao et al., 2012, *J. Pharm. Exper. Ther.* 342:255-262). Among the angiogenic factors, vascular endothelial growth factor (VEGF) is involved in every step of new vessel formation, including the proliferation, migration, invasion, tube formation of endothelial cells, and recruitment of various types of angiogenesis-associated cells, including VEGF receptor 1-positive cells and endothelial progenitor cells (Rafii et al., 2002; Adams and Alitalo, 2007; Ellis and Hicklin, 2008). More recently, we showed that the suppression of tumor growth is mediated, at least in part, by inhibition of the production of VEGF and subsequent tumor angiogenesis (Gao et al., 2011).

Expression and activity of hypoxia-inducible factor 1 (HIF-1) is crucial for the production of VEGF and other angiogenic factors in tumor tissues. HIF-1 is a heterodimeric transcription factor that consists of a constitutively expressed HIF-1α and an inducible α-subunit, HIF-1α. When tumor tissues overgrow, tumor cells located more than 100 µm from vessels are under hypoxic conditions. Because of the oxygen-dependent nature of HIF-1α degradation, low oxygen concentration leads to decreases of protein degradation, resulting in HIF-1α accumulation. On the other hand, some hormones and growth factors, including insulin and lysophosphatidic acid (LPA), also promote protein accumulation of HIF-1α by activating various signaling pathways under normoxic conditions (Cao et al., 2004; Lee et al., 2006, 2009). HIF-1α binds to HIF-1α, translocates into the nucleus, and contributes to tumorigenesis through the transcriptional activation of downstream genes, the protein products of which are required for angiogenesis (including VEGF and angiopoietins), glucose transport, and cell survival (Semenza, 2003; Pouysségur and Mechta-Grigoriou, 2006; Pouysségur et al., 2006). In this example, we examined the effect of L-4F and L-5F on the expression and activity of HIF-1α in human ovarian cancer cell lines and mouse ovarian tumor tissues to delineate the mechanisms behind the antiangiogenic and antitumorigenic effects of apoA-I mimetic peptides.

Cells, Cell Culture, and Reagents.

OV2008 cells were cultured in RPMI 1640 media with 10% fetal bovine serum, penicillin (100 U/ml), streptomycin (100 µg/ml), 1× minimal essential medium nonessential amino acid solution (Invitrogen, Carlsbad, Calif.), and insulin (0.25 U/ml) (Invitrogen). CAOV-3 cells were cultured in complete media consisting of Dulbecco's modified Eagle's medium with high glucose and L-glutamine (2 mM), 10% fetal bovine serum, penicillin (100 U/ml), streptomycin (100 µg/ml), and insulin (0.02 U/ml). To create hypoxic conditions, cells were transferred to a hypoxic chamber (model 3130; Thermo Fisher Scientific, Waltham, Mass.), where they were maintained at 37° C. in an atmosphere containing 5% $CO_2$, 1% $O_2$, and 94% $N_2$. L-4F (the peptide Ac-D-W-F-K-A-F-Y-D-K-V-A-E-K-F-K-E-A-F-$NH_2$ (SEQ ID NO: 12) synthesized from all L amino acids) was dissolved in water at 1 mg/ml (freshly prepared every time) and used between 1 and 10 µg/ml. L-5F was synthesized by Peptisyntha Inc. (Torrance, Calif.), dissolved in ABCT buffer (50 mM ammonium bicarbonate, pH 7.0, containing 0.1 mg/ml Tween 20) at 1 mg/ml, and diluted to the required concentrations before use. Cobalt chloride ($CoCl_2$), insulin, cycloheximide (CHX), and N-(benzyloxycarbonyl)leucinylleucinylleucinal-Z-Leu-Leu-Leu-al (MG-132) were purchased from Sigma-Aldrich (St. Louis, Mo.). LPA (Avanti Polar Lipids, Alabaster, Ala.) in chloroform was dried as recommended by the manufacturer, dissolved in ethanol at a concentration of 20 mM as a stock solution, and diluted to the required concentrations in the corresponding cell culture media before use.

Quantitative Real-Time PCR.

Total RNA was extracted from cells by using a PureLink RNA Mini Kit (Invitrogen). The quantity and quality of RNA were assessed by using a SmartSpec 3000 Spectrophotometer (Bio-Rad Laboratories, Hercules, Calif.). cDNA was synthesized by using the High Capacity cDNA Reverse Transcription Kit (Applied Biosystems, Foster City, Calif.) according to the manufacturer's instructions. PCRs were performed by using the CFX96 realtime PCR system (Applied Biosystems). The cycling conditions were as follows: 3 min at 95° C. followed by 40 cycles of 95° C., 10 s; 60° C., 10 s; 72° C., 30 s followed by a final extension at 72° C. for 10 min. Each 25-µl reaction contained 0.4 µg of cDNA, 12.5 µl of SYBR Green qPCR SuperMix (Bio-Rad Laboratories), and 250 nM forward and reverse primers in nuclease-free water. Primers used were: HIF-1α, 5'-TCC AGT TAC GTT CCT TCG ATC A-3' (SEQ ID NO: 16) and 5'-TTT GAG GAC TTG CGC TTT CA-3' (SEQ ID NO: 17), VEGF, 5'-CGG CGA AGA GAA GAG ACA CA-3' (SEQ ID NO: 18) and 5'-GGA GGA AGG TCA ACC ACT CA-3' (SEQ ID NO: 19); glucose transporter-1, 5'-CGG GCC AAG AGT GTG CTA AA-3' (SEQ ID NO: 20) and 5'-TGA CGA TAC CGG AGC CAA TG-3' (SEQ ID NO: 21); aldolase-A, 5'-TGC TAC TAC CAG CAC CAT GC-3' (SEQ ID NO: 22) and 5'-ATG CTC CCA GTG GAC TCA TC-3' (SEQ ID NO: 23); and GAPDH, 5'-GGA AGG TGA AGG TCG GAG TCA-3' (SEQ ID NO: 24) and 5'-GTC ATT GAT GGC AAC AAT ATC CAC T-3' (SEQ ID NO: 25). The experiment was repeated once with triplicate measurements in each experiment.

Western Blot Analysis.

Western blot analyses were performed as described previously (Gao et al., 2011). In brief, cell lysates were collected in a lysis buffer containing 0.1 MNaCl, 5 mM EDTA, 50 µM sodium orthovanadate, 1% Triton X-100, and protease inhibitor tablet (Roche Diagnostics, Indianapolis, Ind.) in 50 mM Tris buffer, pH 7.5, loaded onto 4 to 12% Bis-Tris gel (Invitrogen), transferred to polyvinylidene difluoride membrane, and incubated with the appropriate antibodies. Anti-pThr$^{202}$/Tyr$^{204}$-Erk, anti-Erk, anti-pThr$^{389}$-p70 S6 kinase, anti-p70 S6 kinase, anti-pSer$^{473}$-Akt, and anti-Akt antibodies were purchased from Cell Signaling Technology (Danvers, Mass.); mouse anti-human HIF-1α antibody was purchased from BD Pharmingen (San Diego, Calif.); rabbit anti-mouse HIF-1α antibody was purchased from Abcam Inc. (Cambridge, Mass.); and anti-GAPDH antibody was purchased from Santa Cruz Biotechnology Inc. (Santa Cruz, Calif.).

Measurement of Cellular Reactive Oxygen Species.

As described previously (Zhou et al., 2007; Lee et al., 2009), OV2008 cells were plated onto a glass slip (Thermo Fisher Scientific) in a 24-well plate at $4 \times 10^4$ cells per well, cultured overnight in normal cultured condition, starved in serum-free media overnight, and treated with L-4F (10 µg/ml) for 1 h. Then, dichlorofluorescein diacetate (DCFHDA, 10 µM) and insulin (200 nM)/$CoCl_2$ (100 µM) were added and incubated with the cells for an additional 0.5 h. The cells were washed twice with phosphate-buffered saline (PBS). The images were captured with a fluorescence microscope (Olympus IX70; Olympus, Tokyo, Japan).

Hypoxia Response Element Reporter Assay.

In brief, OV2008 cells were plated at $2 \times 10^5$ cells per well in a six-well plate and grown in complete media overnight. Then, pGL3-Epo-hypoxia response element (HRE)-Luc plasmid was transfected into cells by using Lipofectamine 2000 (Invitrogen). After 24 h, cells were starved overnight and subjected to L-4F treatment in the presence or absence of stimulators. A reporter assay system (Promega, Madison, Wis.) was used for the measurement of luciferase activity.

Immunofluorescence Staining of HIF-1α.

Immunofluorescence staining was performed as described previously (Lee et al., 2006). In brief, OV2008 cells were plated onto a glass slip (Thermo Fisher Scientific) in 24-well plates at $4 \times 10^4$ cells per well and grown in complete medium overnight. After starvation overnight, cells were subjected to L-4F treatment in the presence or absence of stimulators. Then, cells were fixed in 4% neutral buffered formaldehyde for 25 min at room temperature, permeabilized with 0.5% Triton X-100 in PBS for 10 min, and blocked with 10% normal goat serum, 1% bovine serum albumin, and 0.3 M glycine prepared in PBS for 1 h. Cells were incubated with mouse anti-HIF-1α (1:200) overnight at 4° C. and incubated with Alexa Fluor 568 goat anti-mouse IgG (Invitrogen) for 1 h. Finally, cells were covered with VectaMount solution containing DAPI (Vector Laboratories, Burlingame, Calif.), and images were captured with a fluorescence microscope (Olympus IX70).

In Vivo Tumor Model.

Nine-week-old C57BL/6J female mice were given a 0.5-ml subcutaneous injection of $5 \times 10^6$ ID8 cells prepared as a single cell suspension in PBS mixed with an equal volume of cold Matrigel (BD Biosciences, San Jose, Calif.). After 2 weeks, mice started to receive scrambled 4F peptide (sc-4F) or L-4F (10 mg/kg) by subcutaneous injection at a site distant from the site where the ID8 cells were injected daily for 3 weeks. After 3 weeks, the mice were sacrificed for tumor collection and further analyses.

Immunohistochemistry Staining.

Frozen tumor tissues were sectioned at a thickness of 5 µm and fixed with cold acetone for 10 min at −20° C. The sections were blocked with 10% normal goat serum and 4% bovine serum albumin prepared in PBS for 3 h and immediately incubated with rabbit anti-mouse polyclonal HIF-1α antibody (1:200) (Abcam Inc.) or rat anti-mouse monoclonal CD31 antibody (1:25) (Abcam Inc.) overnight at 4° C. The sections were then incubated with corresponding biotinylated secondary antibodies (Vector Laboratories) for 30 min at room temperature followed by incubation with Vectastain ABC Elite reagents (Vector Laboratories) to visualize the staining. Finally, sections were lightly counterstained with hematoxylin, dehydrated, and coverslipped with Vecta-Mount solution (Vector Laboratories).

Statistics.

Data are shown as mean±S.D. for each group. We performed statistical analyses by unpaired t test. Results for all tests were considered significant if $P<0.05$.

L-4F Inhibits HIF-1α Expression and Angiogenesis In Vivo.

Our previous data showed that the apoA-I mimetic peptides L-4F and L-5F inhibited tumor growth and angiogenesis in an immunocompetent mouse model of ovarian cancer that uses the epithelial cancer cell line ID8 (Gao et al., 2011). Given the importance of HIF-1α in the production of VEGF, a critical growth factor implicated in tumor angiogenesis, we first examined the effect of L-4F on HIF-1α expression by using the same model. Immunohistochemistry staining showed that L-4F treatment decreased HIF-1α expression in tumor tissues compared with a control peptide (sc-4F)-treated group (FIG. 7A). Consistent with our previous report (Gao et al., 2011), we observed a reduction in the number of vessels in L-4F-treated mice compared with the control group (FIG. 7A; see also supplemental materials included in online version of Gao et al., 2012, JPET 342:255-262).

L-4F and L-5F Inhibits HIF-1α Expression in Cell Cultures.

To examine whether L-4F inhibits HIF-1α expression in cells under hypoxic conditions, low oxygen concentration (1% $O_2$) and a hypoxia mimetic chemical, $CoCl_2$, were used to induce HIF-1α expression in a human ovarian cancer cell line, OV2008. Western blot analysis showed that L-4F dose-dependently suppressed hypoxia-induced HIF-1α protein expression (FIG. 7B; see also supplemental materials in online version). Similar results were observed when OV2008 cells were treated with insulin at 100 nM and 200 nM (FIG. 7B) and LPA at 20 µM (see also supplemental materials).

To further confirm the inhibitory role of L-4F in HIF-1α expression, two other human ovarian cancer cell lines, CAOV-3 and SKOV3, were studied. Consistent with the data for OV2008 cells, L-4F dose-dependently inhibited $CoCl_2$- and insulin-induced HIF-1α expression in both CAOV-3 cells (FIG. 7A) and SKOV3 cells.

To examine whether the inhibitory effect on HIF-1α is specific to L-4F, another apoA-I mimetic peptide, L-5F, was used to treat OV2008 cells. Similar to L-4F treatment, L-5F dose-dependently inhibited low oxygen- and $CoCl_2$-stimulated HIF-1α expression (see supplemental materials).

Figure 7:
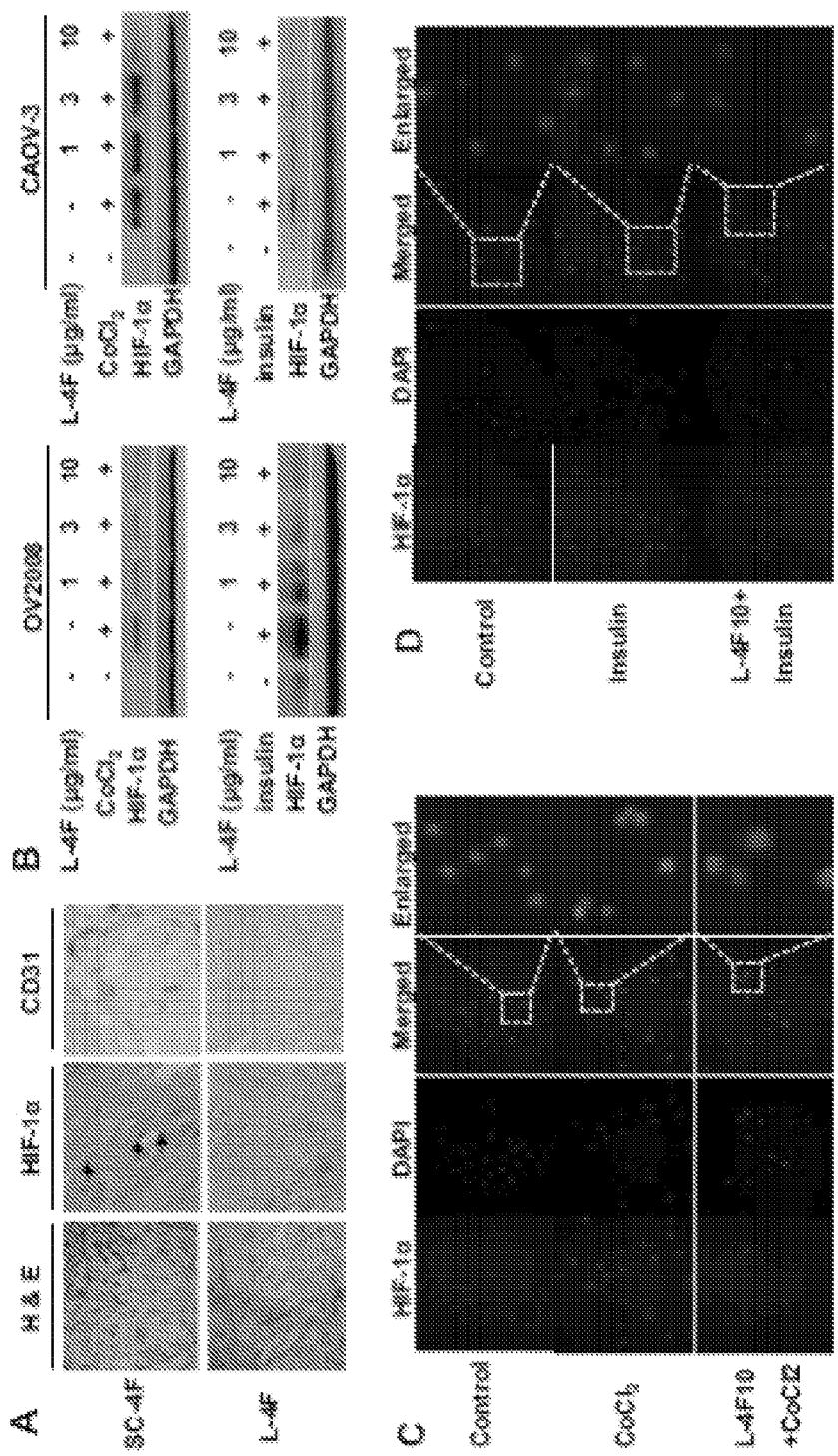
FIGS. 7A-7D. Digital photomicrographs showing that ApoA-I mimetic peptide L-4F inhibits HIF-1α expression in vivo and in vitro.

As a transcription factor, HIF-1α functions in nuclei and activates expression of downstream genes. Immunofluorescence staining was used to examine the effect of L-4F on the nuclear levels of HIF-1α protein. $CoCl_2$ and insulin treatments greatly increased the accumulation of HIF-1α in nuclei of OV2008 cells, and pretreatment of L-4F dramatically reversed these effects (FIGS. 7, C and D).

Inhibition of HIF-1α-Dependent Gene Transcription by L-4F.

Figures 8A, 8C:
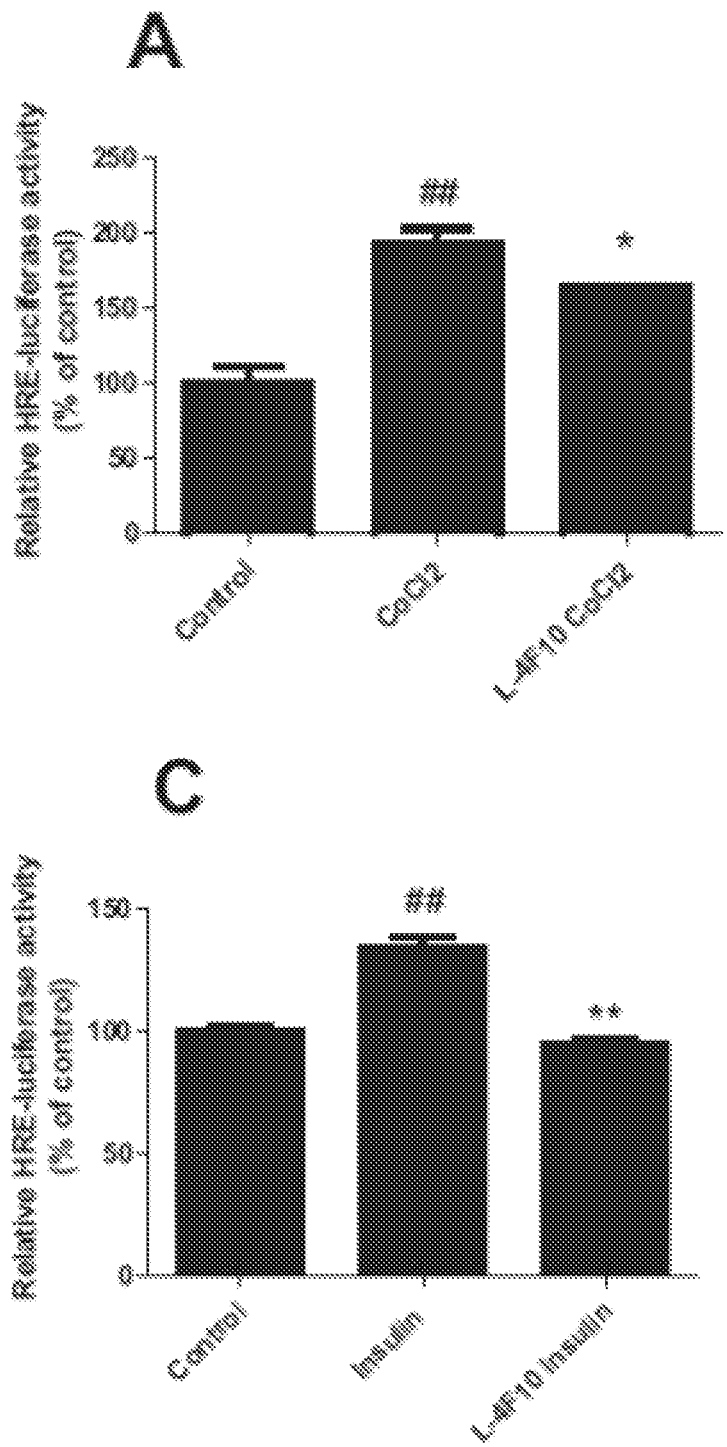
FIGS. 8A-8D. Bar graphs showing that HIF-1α target gene expression is inhibited by L-4F in OV2008 cells.
Figures 8B, 8D:
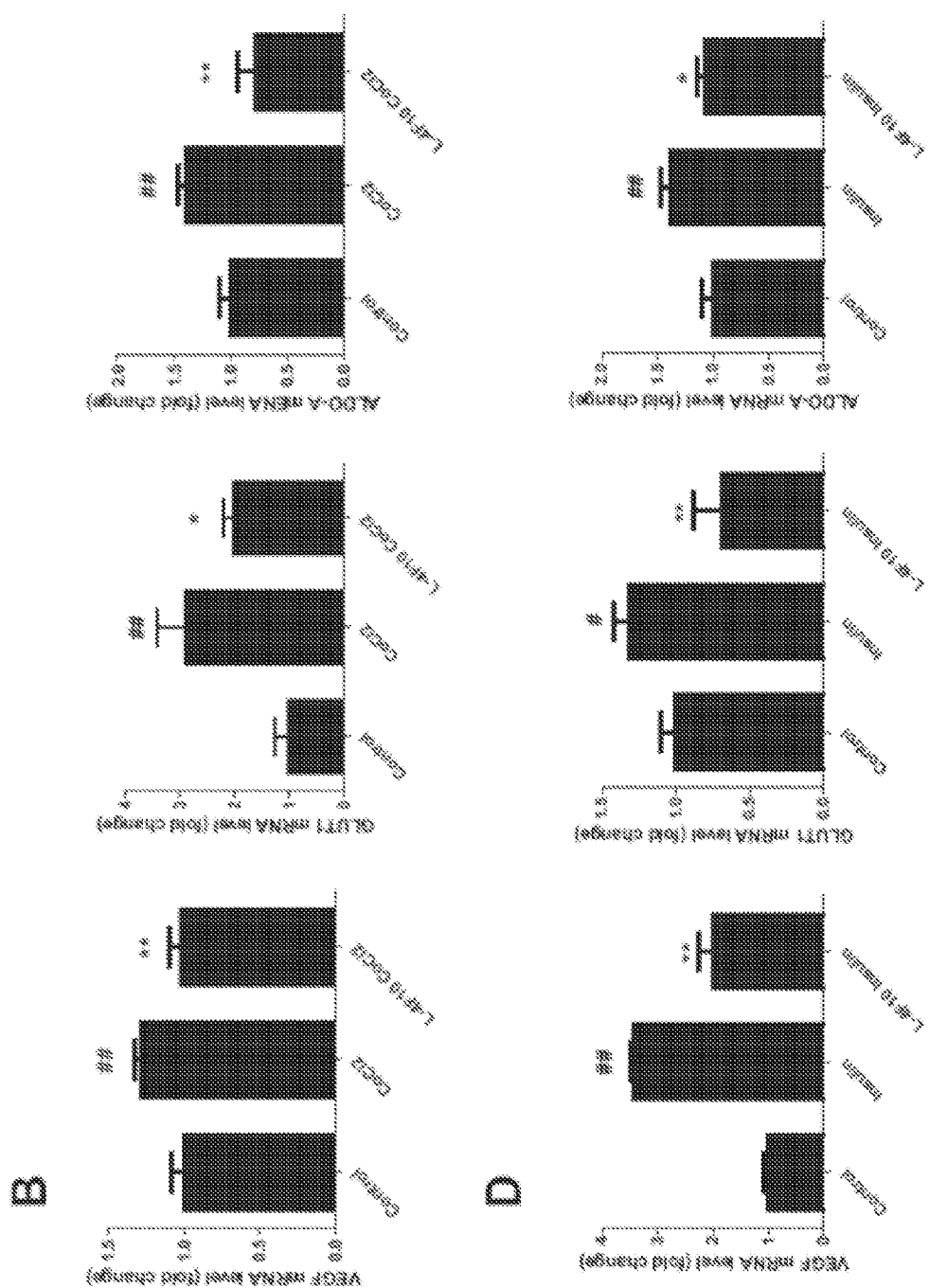

To determine whether L-4F inhibits HIF-1α-driven gene transcription, OV2008 cells were transfected with a HRE containing luciferase reporter plasmid. L-4F treatment significantly inhibited $CoCl_2$- and insulin-mediated induction of luciferase activity (FIGS. 8, A and C). Moreover, L-4F treatment abrogated $CoCl_2$- and insulin-induced increase in mRNA levels of HIF-1α target genes including VEGF, glucose transporter 1, and aldolase-A (FIGS. 8, B and D), suggesting that L-4F inhibits both HIF-1α protein expression and activity.

Post-Treatment of L-4F Decreases HIF-1α Protein Level and Activity in $CoCl_2$- and Insulin-Treated OV2008 Cells.

Figure 9B:
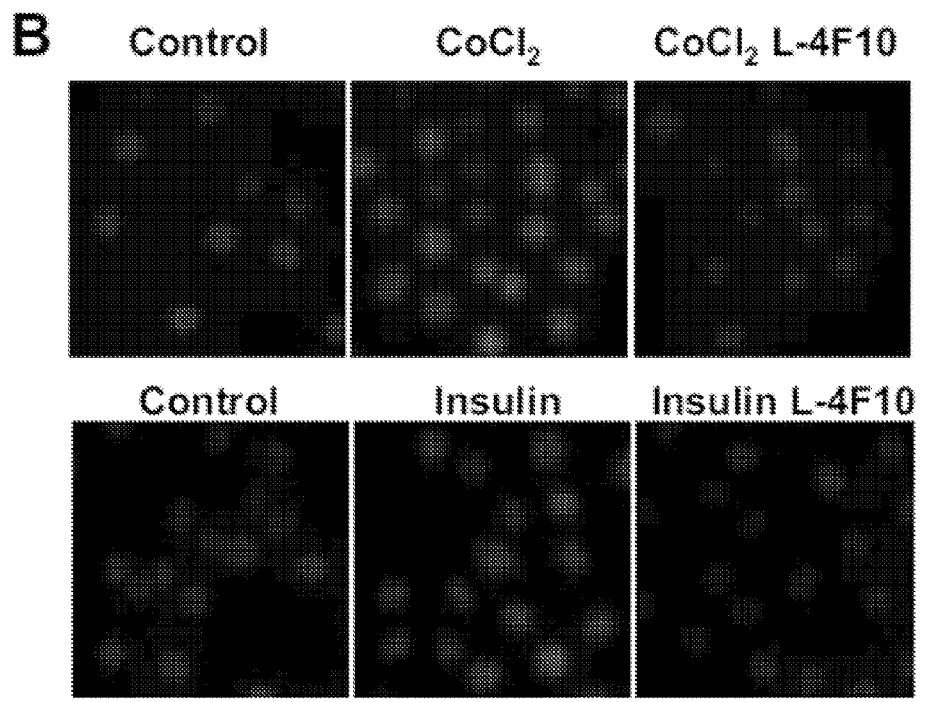

Because HIF-1α expression is elevated in advanced tumors that are presented clinically, we next examined whether L-4F given after hypoxia or growth factor stimulation inhibited HIF-1α expression. OV2008 cells were stimulated first with $CoCl_2$ or insulin for 3 h (see supplemental materials) or 24 h (FIG. 9), and then treated with L-4F for various durations. Post-treatment of L-4F significantly decreased HIF-1α expression in OV2008 cells (FIG. 9A; see also supplemental materials). Immunofluorescence analysis showed decreased nuclear expression of HIF-1α by post-treatment of L-4F (FIG. 9B; see also supplemental materials). Moreover, down-regulation of HIF-1α protein in the nucleus correlated with the inhibition of the transcription of downstream HIF-1α target genes (FIG. 9C; see also supplemental materials).

L-4F does not Affect HIF-1α Transcription.

To determine whether L-4F affects HIF-1α synthesis at the transcriptional level, we quantified HIF-1α mRNA content to determine whether a change in HIF-1α mRNA level precedes that of protein. Real-time RT-PCR analyses indicated that L-4F had no effect on the basal level of HIF-1α mRNA (see supplemental materials). Moreover, consistent with previous reports (Semenza, 2003; Pouysségur et al., 2006; Lee et al., 2009), low oxygen and insulin did not affect HIF-1α gene transcription (see supplemental materials), suggesting that the regulation of HIF-1α protein expression by L-4F occurs at the posttranscriptional level.

L-4F Inhibits S6 Kinase Phosphorylation in an ERKDependent Manner.

Activation of S6 kinase is critical for insulin-induced de novo synthesis of HIF-1α (Semenza, 2003). To determine the molecular mechanism of HIF-1α inhibition by L-4F, we tested whether L-4F affects the insulin-stimulated protein synthesis of HIF-1α. Our data showed that L-4F at 10 µg/ml prevented phosphorylation of S6 kinase (FIG. 10A). S6 kinase phosphorylation is regulated by the activation of upstream signaling molecules ERK and Akt. As shown in FIG. 10B, L-4F inhibited activation of ERK1/2, but had no effect on the phosphorylation of Akt, except at 0.5 h, suggesting that the inhibition of S6 kinase activation may most likely be a result of the suppression of ERK phosphorylation. It is noteworthy that we did not observe an effect of $CoCl_2$ on the phosphorylation of ERK, Akt, and S6 kinase in OV2008 cells (see supplemental materials). This result is not surprising because $CoCl_2$ treatment mimics hypoxia, which leads to decreases in HIF-1α protein degradation (Pouyssé-gur and Mechta-Grigoriou, 2006).

L-4F Treatment Promotes Proteasome-Dependent Protein Degradation.

Figure 11B:
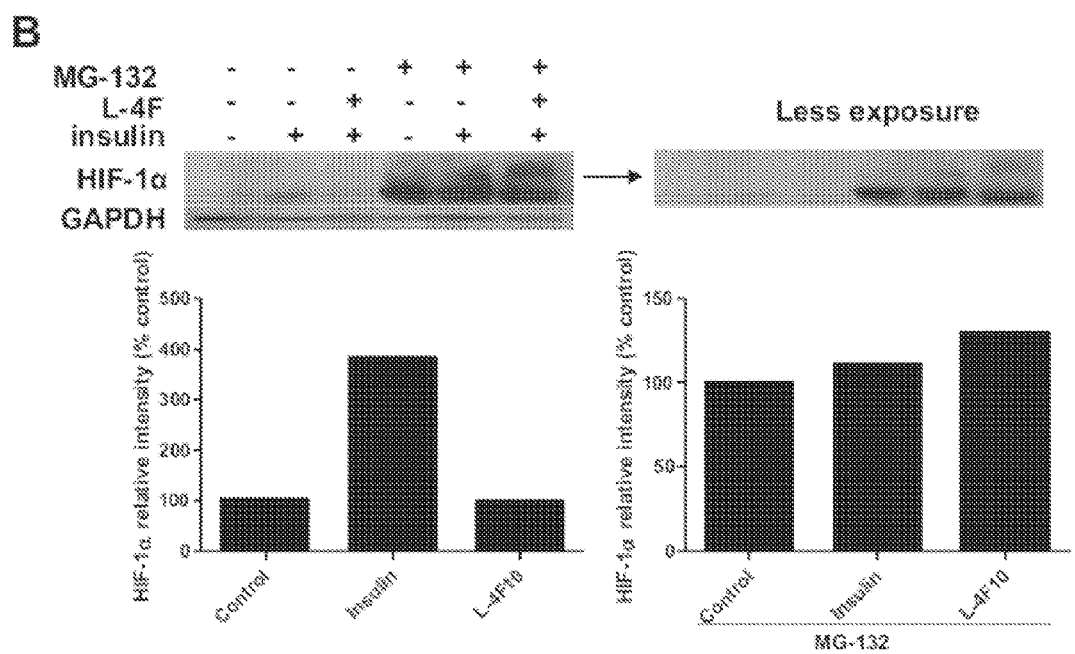

We next examined whether L-4F changes the stability of the HIF-1α protein. CHX, a compound that prevents new protein synthesis, was used to inhibit de novo HIF-1α protein synthesis. Our data showed that OV2008 cells treated with CHX in combination with insulin exhibited a gradual decrease in HIF-1α as a function of time, and simultaneous L-4F treatment accelerated the degradation of HIF-1α protein (FIG. 11A). We observed a similar effect of L-4F on $CoCl_2$-treated OV2008 cells (see supplemental materials). Furthermore, MG-132, a proteasome inhibitor, led to a reversal of the inhibitory effect of L-4F on insulin-mediated HIF-1α expression (FIG. 11B). These results suggest that L-4F inhibits insulin- and $CoCl_2$-induced HIF-1α expression and activity in ovarian cancer cells, in part, by accelerating the degradation of HIF-1α protein.

Inhibition of Insulin- and $CoCl_2$-Induced ROS Production by L-4F Treatment.

It is reported that insulin treatment (Zhou et al., 2007; Lee et al., 2009) and $CoCl_2$ treatment (Chandel et al., 2000; Griguer et al., 2006) significantly increase cellular ROS levels, which subsequently promotes the synthesis of HIF-1α and inhibits its degradation. As shown by dichlorofluorescein oxidation assay (FIG. 12), treatment of insulin and $CoCl_2$ led to an increase of cellular ROS levels in OV2008 cells. Pretreatment of L-4F dramatically prevented the cellular ROS production induced by insulin and $CoCl_2$ (FIG. 12), suggesting that the inhibitory role of L-4F on HIF-1α expression may be a result of the inhibition of ROS accumulation.

Discussion

Figure 9D:
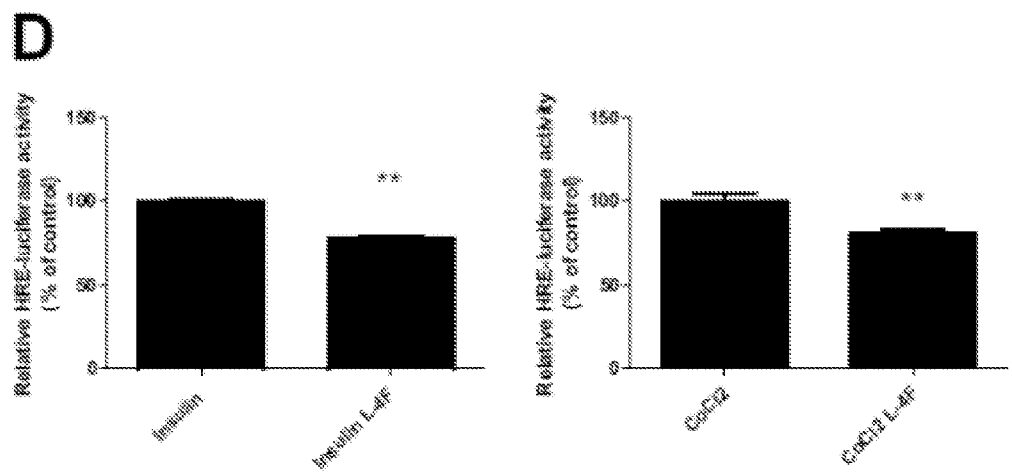

HIF-1 is a key cellular survival protein under hypoxia and is associated with tumor progression and metastasis in various solid tumors (Seeber et al., 2011). Targeting HIF-1α could be an attractive anticancer therapeutic strategy (Semenza, 2003; Belozerov and Van Meir, 2005; Seeber et al., 2011). Expression of HIF-1α is increased by both hypoxic and nonhypoxic stimuli. Low oxygen concentration or treatment with $CoCl_2$, a hypoxic mimetic compound, inhibits the degradation of HIF-1α and increases HIF-1α protein stability and accumulation. Some growth factors, including insulin and LPA, also promote post-transcriptional protein synthesis and up-regulate the expression and activity of HIF-1α (Semenza, 2003; Pouysségur and Mechta-Grigoriou, 2006; Pouysségur et al., 2006). In this article, we demonstrate that: 1) L-4F inhibits HIF-1α expression in mouse tumor tissues (FIG. 7A); 2) pretreatment and post-treatment of L-4F and L-5F decrease low oxygen-, $CoCl_2$-, insulin-, and LPA-induced expression and nuclear levels of HIF-1α in human ovarian cancer cell lines (FIGS. 7 and 9; see also supplemental materials); and 3) L-4F inhibits $CoCl_2$- and insulin-stimulated expression of HRE-driven reporter gene and activation of HIF-1α target genes (FIGS. 8 and 9; see also supplemental materials). Real-time RT-PCR analyses indicated that L-4F has no effect on HIF-1α gene transcription in OV2008 cells (see supplemental materials), indicating that the regulation of HIF-1α protein by L-4F occurs at the post-transcriptional level.

Figure 12A:
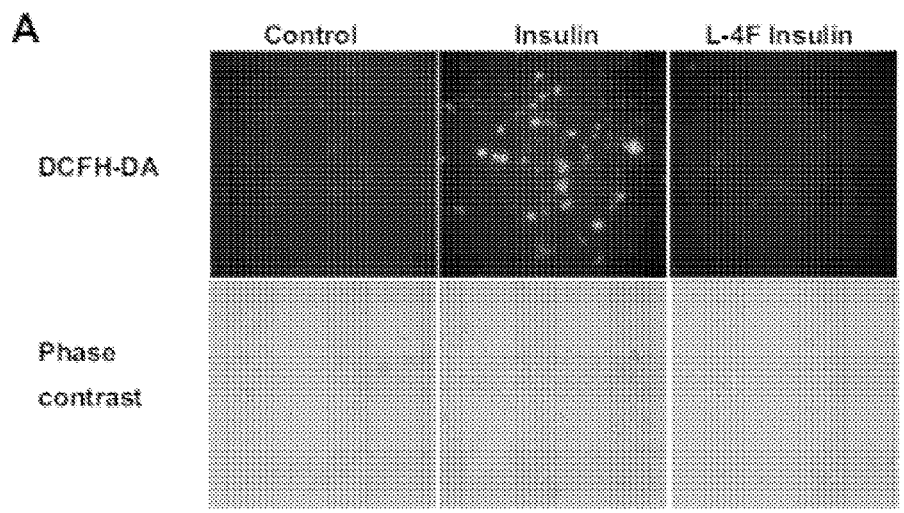
FIGS. 12A-12B. Effect of L-4F on $CoCl_2$- and insulin-stimulated ROS production. OV2008 cells were pretreated with L-4F (10 μg/ml) for 1 h, and then treated with insulin (200 nM)/$CoCl_2$ (100 μM) and DCFH-DA (10 μM) for 30 min. After washing cells twice with PBS, images of cells were captured with a fluorescence microscope. Representative figures are shown at the original magnification of 200×.
Figure 12B:
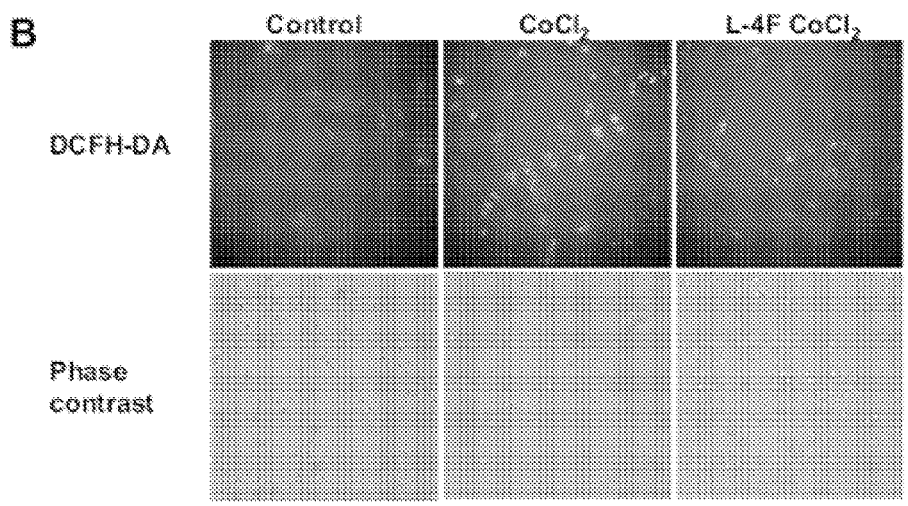

There is compelling evidence that ROS are key players in the regulation of HIF-1α under normoxia as well as hypoxia (Pouysségur and Mechta-Grigoriou, 2006). As reported previously, treatment of cells with low oxygen concentration (Chandel et al., 2000; Guzy et al., 2005; Guzy and Schumacker, 2006), $CoCl_2$ (Chandel et al., 2000; Griguer et al., 2006), insulin (Zhou et al., 2007; Lee et al., 2009), and LPA (Chen et al., 1995; Saunders et al., 2010) lead to ROS generation. ROS production is critical for HIF-1α expression in cells, and removal of ROS impairs HIF-1α accumulation induced by hypoxia and insulin (Brunelle et al., 2005; Mansfield et al., 2005; Carnesecchi et al., 2006; Biswas et al., 2007). Ganapathy et al. (2012) reported that D-4F, an apoA-I mimetic peptide, significantly decreases the production of superoxide and $H2O2$ and improves the oxidative status on ID8 cells. However, it is unknown whether peptide treatment affects hypoxia- or growth factor-mediated ROS production. Here, we report that L-4F treatment dramatically inhibits insulin- and $CoCl_2$-induced ROS production in OV2008 cells (FIG. 12). Furthermore, L-4F accelerated HIF-1α degradation in cancer cells exposed to insulin and $CoCl_2$ (FIG. 11A; see also supplemental materials). MG-132, a 26S proteasome inhibitor, reversed the inhibitory effect of L-4F on insulin-mediated HIF-1α expression (FIG. 11B). Taken together, these data demonstrate that L-4F decreases the protein stability of HIF-1α and inhibits the accumulation of transcriptionally active HIF-1α, at least in part, through its ROS-scavenging effect.

In an effort to find the molecular mechanism of HIF-1α inhibition, we determined whether L-4F affects the synthesis of HIF-1α protein. Insulin activates receptor tyrosine kinase and downstream signaling molecules, most notably S6 kinase, leading to increases of mRNA translation and de novo synthesis of HIF-1α (Treins et al., 2002; Semenza, 2003). L-4F inhibits insulin-stimulated phosphorylation of S6 kinase at various time points, resulting in a decrease of HIF-1α protein level (FIG. 10A). Further experiments showed that down-regulation of S6 kinase activity may be a result of the inhibition of the activation of ERK1/2, but not Akt (FIG. 10B). It is noteworthy that it is reported that ROS is involved in insulin-stimulated phosphorylation of ERK1/2 and S6 kinase, but not Akt (Zhou et al., 2007), indicating that ROS removal may also be involved in the inhibition of the de novo synthesis of HIF-1α by L-4F.

Previous reports showed that D-4F (an apoA-I mimetic peptide identical to L-4F but synthesized with all D amino acids) increases the expression and activity of two antioxidant enzymes, heme oxygenase 1 and extracellular superoxide dismutase (SOD), in aorta from control and diabetic rats (Kruger et al., 2005). More recently, we also demonstrated that D-4F up-regulates the antioxidant enzyme Mn-SOD in ID8 cells, and knockdown of Mn-SOD results in the complete loss of antitumorigenic effects of D-4F in a mouse ovarian cancer model (Ganapathy et al., 2012). Because SOD activity modulates ROS production and cellular oxidative stress, induction of SOD may be an important part of the mechanism of action of apoA-I mimetic peptides.

In conclusion, our data demonstrate that apoA-I mimetic peptides inhibit the expression and activity of HIF-1α both in vivo and in cell culture. The inhibition of HIF-1α may be a critical mechanism responsible for the suppression of tumor progression by apoA-I mimetic peptides.

References

A complete list of citations to references provided throughout Example 4 can be found in Gao et al., 2012, *J. Pharm. Exper. Ther.* 342:255-262. The online version of this article also contains supplemental materials referenced in Example 4.

Example 5

HDL Mimetics Inhibit Tumor Development in Both Induced and Spontaneous Mouse Models of Colon Cancer This example demonstrates that HDL mimetics, L-4F (an apolipoprotein A-I mimetic peptide) and G* (an apolipoprotein J mimetic peptide) affect tumor growth and development in mouse models of colon cancer. HDL mimetics reduced viability and proliferation of CT26 cells, a mouse colon adenocarcinoma cell line, and decreased CT26 cell-mediated tumor burden in BALB/c mice when administered subcutaneously or orally. Plasma levels of lysophosphatidic acid (LPA), a serum biomarker for colon cancer, were significantly reduced in mice that received HDL mimetics, suggesting that binding and removal of proinflammatory lipids is a potential mechanism for the inhibition of tumor development by HDL mimetics. Furthermore, L-4F significantly reduced size and number of polyps in APC$^{min/+}$ mice, a mouse model for human familial adenomatous polyposis, suggesting that HDL mimetics are effective in inhibiting the development of both induced and spontaneous cancers of the colon. These results identify HDL mimetics as a novel therapeutic strategy for the treatment of colon cancer.

Mice

The Animal Research Committee at University of California at Los Angeles approved all mouse protocols. Six-week-old BALB/c female mice and 6-week-old C57BL/6J-APC$^{min/+}$ male mice were purchased from The Jackson Laboratory.

Peptides

HDL mimetics, the apoA-I peptide L-4F (Ac-D-W-F-K-A-F-Y-D-K-V-A-E-K-F-K-E-A-F-NH$_2$; SEQ ID NO: 12) and a scrambled peptide (sc-4F) containing the same amino acids as in the 4F peptides but arranged in a sequence (Ac-D-W-F-A-K-D-Y-F-K-K-A-F-V-E-E-F-A-K-NH$_2$; SEQ ID NO: 13) that prevents the formation of a class A amphipathic helix, and the apoJ mimetic, named G* peptide {Ac-L-V-G-R-Q-L-E-E-F-LNH$_2$ (SEQ ID NO: 26) corresponding to amino acids 113 to 122 in apoJ (L-[113-122]apoJ)}, were synthesized from all L-amino acids. The peptides were dissolved in H$_2$O for administration by injection. For administration of peptides in the diet, the peptides were mixed into standard mouse chow (Ralston Purina) using techniques essentially as described previously for a Western diet (18). However, the Western diet was not administered in any of the experiments reported here; the mice only received standard mouse chow with or without the peptides.

Cell Culture Experiments

CT26 cell line derived from N-nitroso-N-methyl urethane-induced mouse colon carcinoma of BALB/c origin was purchased from the American Type Culture Collection. CT26 cells (2,000 cells per well) were first cultured in complete medium in 96-well culture plates, and 24 hours later the medium was replaced with serum-free medium. Following an overnight incubation, the cells were either treated with vehicle (control) or treated with 10 mg/mL of either L-4F or G* peptide. The peptides were dissolved in H$_2$O. Cells were incubated for an additional 48 hours and assayed for viability using the MTS assay kit (Promega) according to the manufacturer's protocol. For proliferation assay, cells were labeled with bromodeoxyuridine (BrdUrd) for the last 4 hours of the 48 hours incubation. Cells were subsequently washed, fixed, and incubated with mouse anti-BrdUrd antibody for 1 hour at room temperature and detected by a peroxidase-coupled goat anti-mouse secondary antibody (Calbiochem). Absorbance was measured using dual wavelengths 450 and 540 nm.

Tumor Load Study

Six-week-old BALB/c female mice were given a 100 mL subcutaneous injection of 1×10$^6$ CT26 cells prepared as a single cell suspension in PBS, and the mice were treated with sc-4F or L-4F at 10 mg/kg administered subcutaneously daily for 15 days. The mice were sacrificed and tumor weights were measured.

Pulmonary Metastasis In Vivo

BALB/c mice were intravenously injected with 2×10$^4$ CT26 cells in 100 mL of PBS via tail vein injection and the mice were treated with L-4F or sc-4F at 10 mg/kg/d administered subcutaneously for 3 weeks, or treated with sc-4F or L-4F or G* peptide at 100 mg/kg/d administered in a chow diet for 3 weeks. After 3 weeks treatment, the mice were sacrificed; lungs were harvested, weighed, and fixed with Bouin solution (Sigma). Tumor nodules on the lung surface were counted.

APC$^{min/+}$ Mice Study

Six-week-old APC$^{min/+}$ male mice on a C57BL/6J background were treated with L-4F or sc-4F at 100 mg/kg/d administered in a chow diet. After 8 weeks treatment, mice were sacrificed. The entire intestine was immediately removed, fixed in formalin and 70% ethanol. The intestine was opened and examined under a dissecting microscope to count and measure the tumors.

Immunohistochemistry Staining

Tumor tissues from the lung surface were fixed and embedded with paraffin, sectioned at 5 mm thickness. Sections were deparaffinized with xylene, rehydrated with 100%, 90%, 70%, and 50% ethanol, treated with proteinase K at 20 mg/mL for 30 minutes, and treated with 3% H$_2$O$_2$ for 30 minutes at room temperature to inhibit endogenous peroxidase, blocked with 10% normal goat serum and 4% bovine serum albumin prepared in PBS for 3 hours, and then incubated with 1:50 rat antimouse monoclonal CD31 antibody overnight at 4° C. The sections were incubated with corresponding biotinylated secondary antibody for 1 hour, followed by incubation with Vectastain ABC Elite reagents.

Cell-Cycle Analysis

CT26 cells were cultured in 6-well plates overnight and then serum starved for 48 hours. Cells were either treated with vehicle (control), or treated with 10 mg/mL of L-4F or G*peptide, and incubated for an additional 48 hours. Cells were collected, washed with PBS, and fixed with 70% ice-cold methanol overnight at 4° C. The fixed cells were collected by centrifugation, washed with PBS, and resuspended in 0.3 mL of PBS containing 40 mg/mL RNaseA and 100 mg/mL propidium iodide, and subjected to flow cytometric cell-cycle analysis by FACScan from BD Biosciences.

Western Blot Analysis

Total cell proteins were collected after treatment in cell lysis buffer containing 0.1 mol/L NaCl, 5 mmol/L EDTA, 50 mmol/L sodium orthovanadate, 1% Triton X-100, and protease inhibitor tablet in 50 mmol/L Tris buffer (pH 7.5). Twenty micrograms of total proteins were separated by SDS-PAGE and transferred onto nitrocellulose membrane and followed by incubation with primary antibody at 4° C. in 5% skim milk and 0.1% Tween-20. Anti-cyclin D1 and anti-cyclin A rabbit polyclonal antibodies were used at 1:1,000 dilution, and anti-b-actin polyclonal antibody was used at 1:2,000 dilution.

ELISA Analysis

Interleukin (IL)-6 concentrations were measured in plasma by a competition ELISA according to the manufacture's protocol (Invitrogen).

LPA Binding Affinity and Serum LPA Levels

LPA (20:4) was purchased from Avanti Polar Lipids. LPA levels were determined as described previously (19).

Statistical Analyses

The data are shown as means±SD for each group. We carried out statistical analyses by unpaired t test. All results were considered statistically significant at P<0.05.

Figures 13A, 13B, 13C, 13D, 13E, 13F:
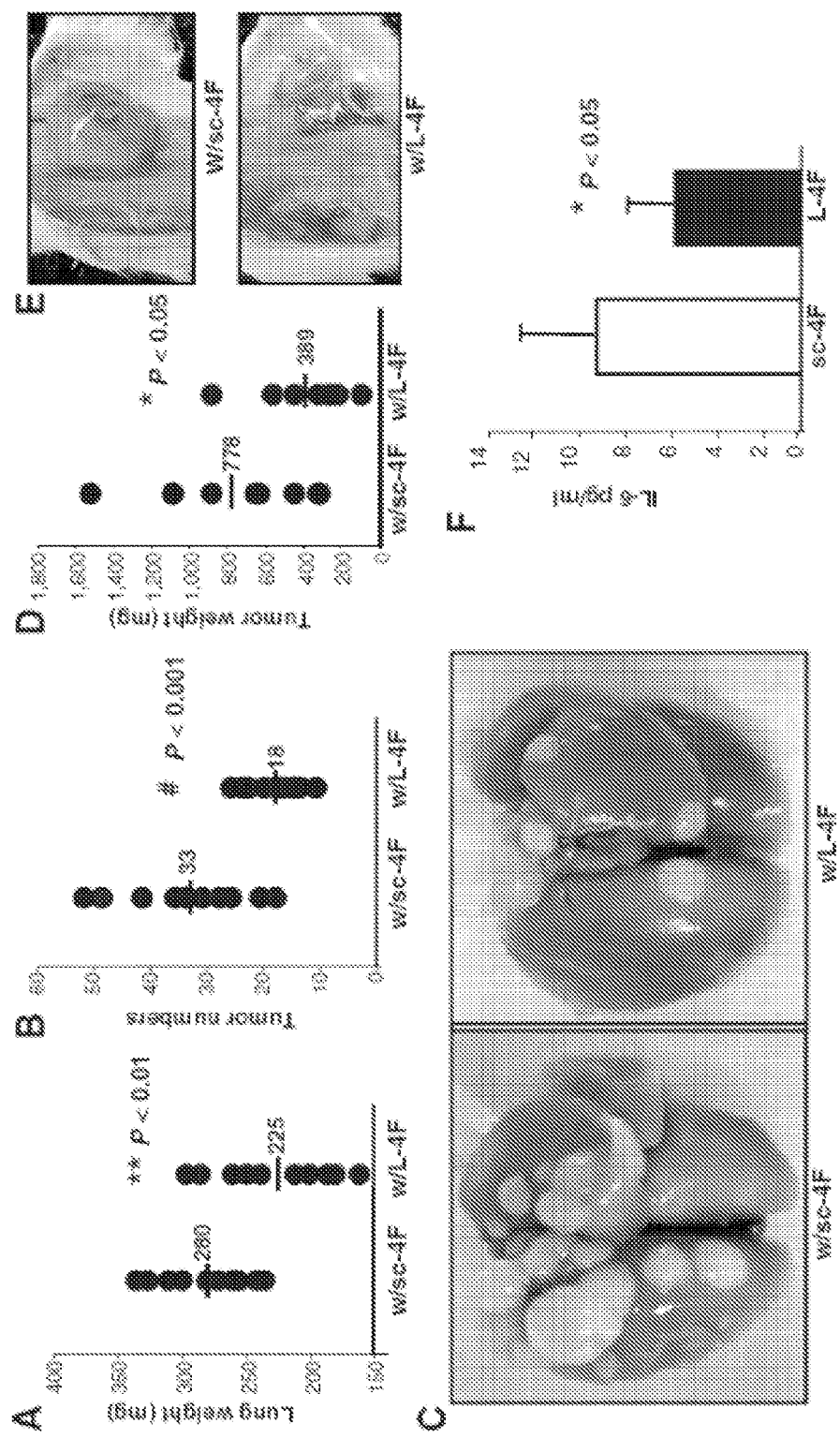
FIGS. 13A-13F. CT26 cell-mediated lung tumors and flank tumors are significantly decreased in BALB/c mice treated with HDL mimetic, L-4F by subcutaneously. Lung tumors were established in BALB/c mice (n=11 per group) as described in Example 5. Mice were sacrificed 3 weeks after CT26 cells were administered by tail vein injection. Lungs were harvested and weighed. Lung tumors were counted.

HDL Mimetic L-4F Inhibits Tumor Development Following CT26 Cell Injection in BALB/c Mice CT26 is a colon adenocarcinoma cell line that develops metastatic pulmonary tumors when introduced intravenously into immunocompetent BALB/c mice (20-22). CT26 cell line has been widely used as a syngeneic tumor model to study therapeutic applications for cancer in mouse models and therefore we chose CT26 cells for the colon cancer study in our HDL mimetic studies. We first examined the effect of L-4F and sc-4F (a scrambled peptide containing the same amino acids as in the 4F peptide but arranged in a sequence that prevents the formation of a class A amphipathic helix) administered subcutaneously at 10 mg/kg/d for 3 weeks on lung tumor formation in BALB/c mice injected with $2 \times 10^4$ CT26 cells via tail vein. The lung weights (FIG. 13A) and the tumor numbers counted on the lung surface (FIG. 13B) in BALB/c mice treated with L-4F (n=11 per group) were significantly reduced compared with mice treated with sc-4F (280 vs. 225 mg, P<0.01; 33 vs. 18, P<0.001). Representative photographs of lung tumors from the 2 groups are shown in FIG. 13C. We next examined whether L-4F treatment effects the development of tumors in the flanks of BALB/c mice. Six-week-old BALB/c female mice were injected with $1 \times 10^6$ CT26 cells subcutaneously in the flank. The mice were treated with either sc-4F (n=9) or L-4F (n=8) at 10 mg/kg administered subcutaneously daily for 15 days at a site distant from the site where the CT26 cells were injected. The flank tumor weights were significantly larger in BALB/c mice treated with sc-4F compared with mice treated with L-4F (778 vs. 389 mg, P<0.05; FIG. 13D). Representative photographs of flank tumors from the 2 groups are shown in FIG. 13E. We also measured IL-6 levels in plasma from the experiment shown in FIG. 13A. IL-6 was significantly decreased in mice with L-4F treatment compared with control group (FIG. 13F).

Figures 14A, 14B, 14C, 14D:
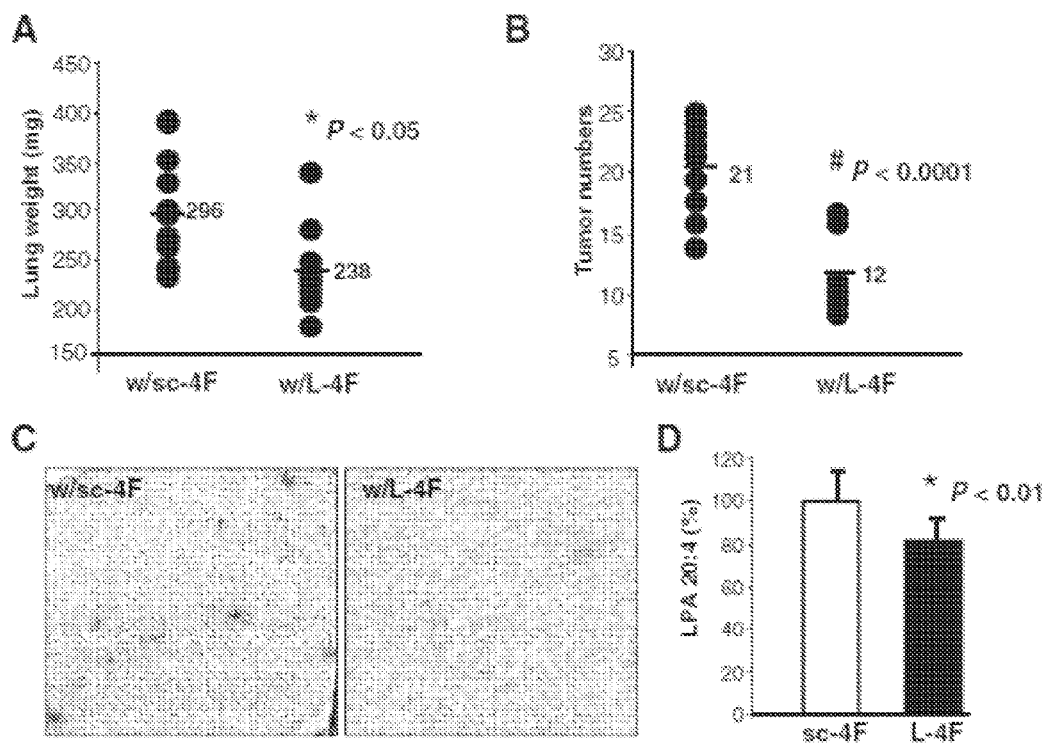
FIGS. 14A-14D. CT26 cell-mediated lung tumors are significantly decreased in BALB/c mice treated with L-4F administered in mouse chow. Lung tumors were established in BALB/c mice as described in Example 5. Mice were sacrificed 3 weeks after CT26 cells were administered by tail vein injection. Lungs were harvested and weighed. Lung tumors were counted.

Tumor Development Following CT26 Cell Injection is Significantly Decreased in Mice that were Treated with L-4F Administered in Mouse Chow We recently reported that 4F is effective in animal models of atherosclerosis whether administered subcutaneously or orally (18). To determine whether L-4F could reduce tumor development when administered orally, BALB/c mice were injected with $2 \times 10^4$ CT26 cells via tail vein and treated with L-4F (n ¼=9) or sc-4F (n=12) at 100 mg/kg/d administered in the chow diet for 3 weeks. The lung weights (FIG. 14A) and the tumor numbers (FIG. 14B) in BALB/c mice treated with sc-4F were significantly larger compared with mice treated with L-4F (296 vs. 238 mg, P<0.05; 21 vs. 12, P<0.0001). We previously reported that L-4F inhibits angiogenesis in vivo (23). Immunohistochemical staining of tumor sections from this experiment showed a significant decrease in CD31 expression in tumors derived from mice treated with L-4F compared with control mice (FIG. 14C). Furthermore, plasma LPA levels were significantly reduced in mice receiving L-4F peptide compared with their corresponding control mice, P<0.01 (FIG. 14D).

Figures 15A, 15B, 15C:
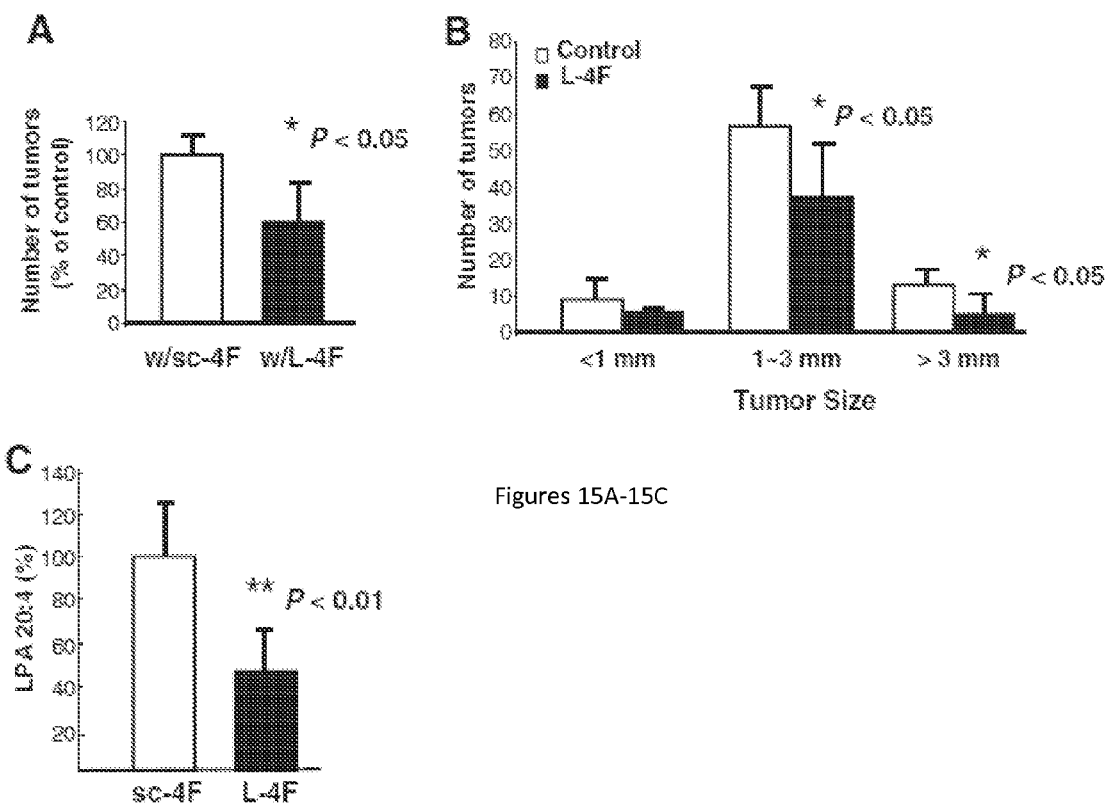
FIGS. 15A-15C. Effect of L-4F treatment in chow diet on tumor number and size in the intestinal tract of C57BL/6J-$APC^{min/+}$ mice. $APC^{min/+}$ mice were sacrificed after 8 weeks treatment with sc-4F or L-4F administered in mouse chow as described in Example 5.

Tumor Numbers and Sizes in the Intestinal Tract are Significantly Decreased in C57BL/6J-Apc$^{min/+}$ Mice Treated with L-4F Administered in Mouse Chow We next examined whether HDL mimetics could affect the development of colon tumors in a spontaneous model of colon cancer. APC$^{min/+}$ mouse is an established mouse model for colon cancer and mirrors the development of familial adenomatous polyposis in humans (24, 25). Six-week-old C57BL/6J-Apc$^{min/+}$ male mice were treated with L-4F (n=5) or sc-4F (n=6) at 100 mg/kg administered in mouse chow for 8 weeks. The tumor numbers and sizes in the intestinal tract from mice treated with L-4F were significantly reduced compared with mice treated with sc-4F (100% vs. 60%, P<0.05; 1-3 mm: 56.5 vs. 36.8, P<0.05; >3 mm: 12.8 vs. 5, P<0.05; FIGS. 15A and 15B). Plasma LPA levels from this experiment were significantly reduced in mice receiving L-4F peptide compared with to control mice, P<0.01 (FIG. 15C).

Figures 16A, 16B, 16C, 16D:
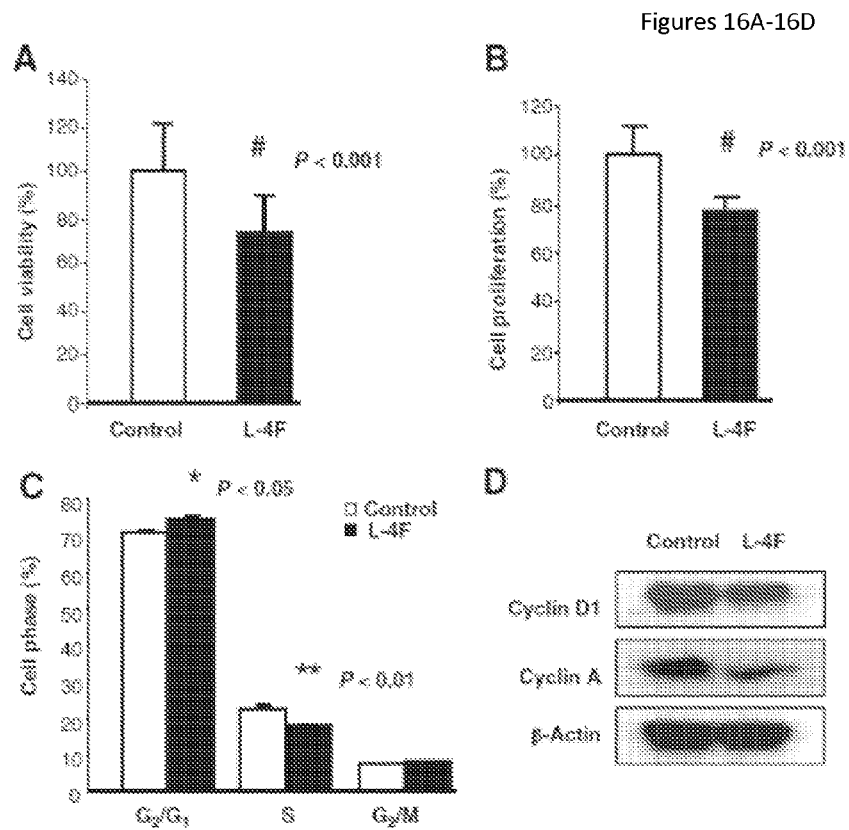
FIGS. 16A-16D. HDL mimetic, L-4F reduces viability, inhibits proliferation, and affects cell cycle and cyclin proteins in CT26 cells. CT26 cells were cultured as described in Example 5 and incubated with either vehicle (control) or L-4F at a concentration of 10 mg/mL.

L-4F Alters CT26 Cell Viability, Proliferation, Cell Cycle, and Expression of Cell-Cycle-Related Proteins In Vitro To examine the mechanisms by which HDL mimetic, L-4F, inhibits CT26 cell-mediated tumor development in mice, the effect of L-4F on CT26 cell viability was determined in vitro. Cell viability was reduced by more than 25% (P<0.001) in CT26 cells that were treated with L-4F (10 mg/mL) when compared with control (FIG. 16A). Moreover, L-4F significantly inhibited proliferation of CT26 cells (P<0.001) as measured by BrdUrd incorporation (FIG. 16B). To investigate whether L-4F inhibited cell proliferation through changes in cell-cycle progression, the effect of L-4F on the cell-cycle profile was assessed in CT26 cells. Cell-cycle analysis showed that L-4F treatment for 48 hours induced an increase in G0/G1 phase and arrest in S phase (FIG. 16C). Moreover, Western blot analysis showed that expression of the cell-cycle proteins cyclin D1 and cyclin A were significantly lower in cells treated with L-4F (FIG. 16D).

HDL Mimetic L-4F Inhibits LPA-Induced Viability of CT26 Cells

Figures 17A, 17B:
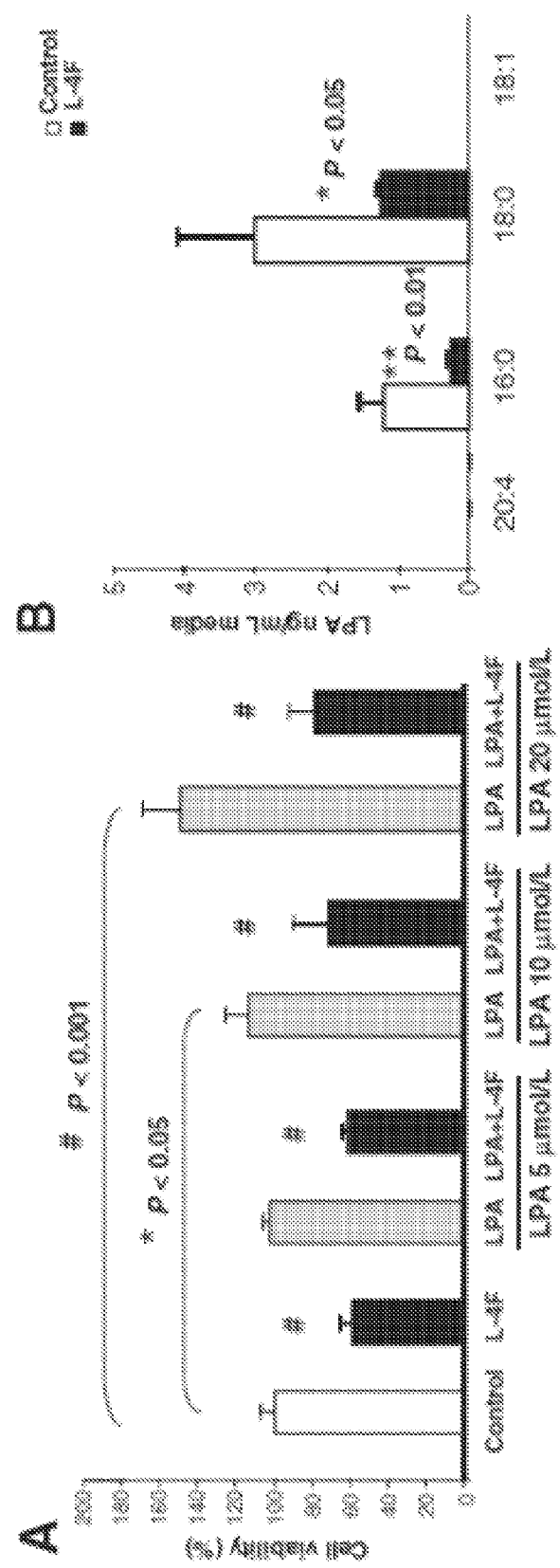
FIGS. 17A-17B. HDL mimetic, L-4F inhibits LPA induced viability of CT26 cells and reduces LPA levels in cell culture medium.

LPA has been identified as an important mediator of tumor development, progression, and metastases in humans (26, 27). We have previously shown that apoAI mimetic peptides inhibit LPA-induced viability of ID8 cells and reduce serum LPA levels in mice injected with ID8 cells (17). L-4F binds LPA (17), as expected, LPA (10-20 mmol/L) significantly improved CT26 cell growth, and L-4F significantly reduced LPA-induced viability at all doses tested, P<0.001 (FIG. 17A). We measured LPA levels in cell culture medium by liquid chromatography-mass spectrometry and found that LPA 16:0 and 18:0 were significantly decreased with L-4F treatment compared with the control medium. LPA 20:4 and 18:1 were not detectable in cell culture medium (FIG. 17B).

Figures 18A, 18B, 18C, 18D, 18E:
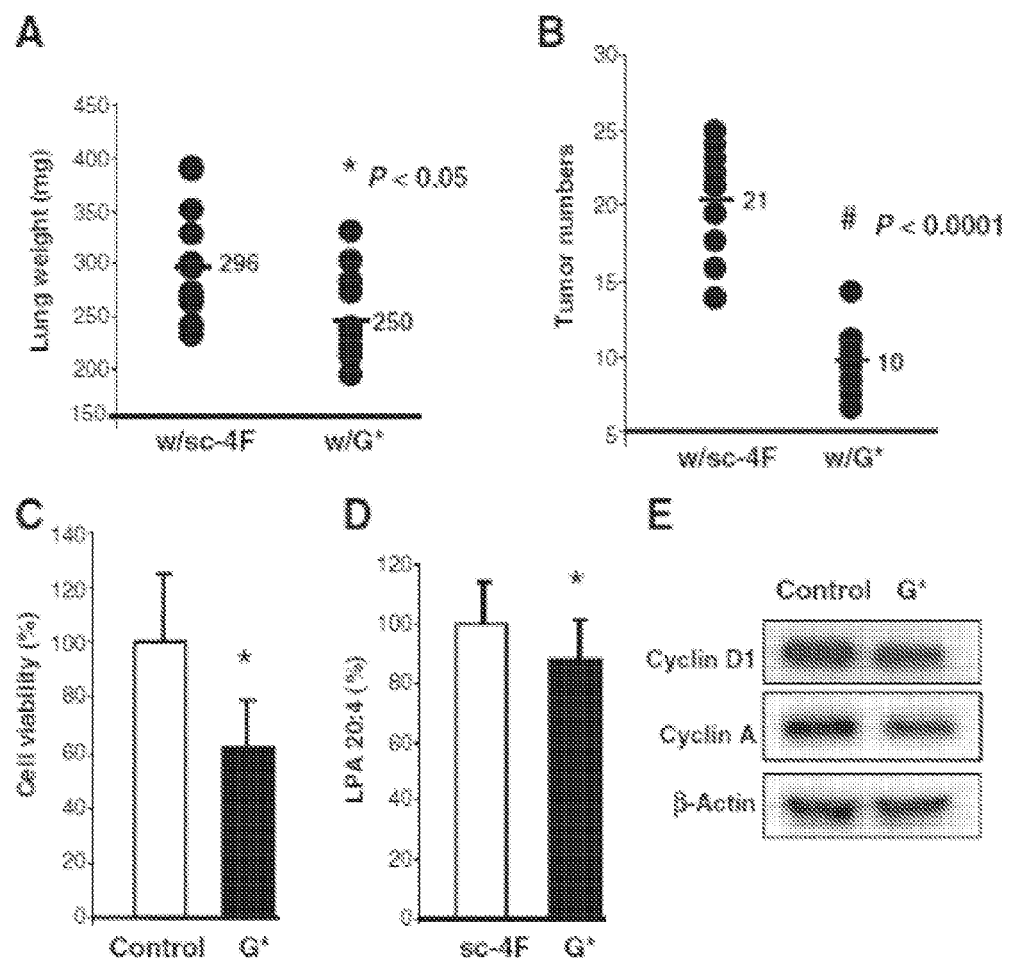
FIGS. 18A-18E. G* (L-[113-122]apoJ) peptide has effects similar to L-4F in vivo and in vitro. Lung tumors were established in BALB/c as described in Example 5. Mice were sacrificed 3 weeks after CT26 cells were injected into the tail vein. Lungs were harvested and weighed. Lung tumors were counted.

HDL Mimetic, G* Peptide (L-[113-122]apoJ) Inhibits CT26 Cell Growth and CT26-Mediated Tumor Development G* (L-[113-122]apoJ) peptide was used to repeat the studies in vivo and in vitro. Pulmonary tumor development following CT26 cell injection was significantly decreased in mice treated with G* peptide at 100 mg/kg/d administered in mouse chow for 3 weeks (Lung weights were 296 vs. 250 mg, P<0.05; tumor numbers were 21 vs. 10, P<0.0001; FIGS. 18A and 18B). Cell viability was approximately 40% lower in CT26 cells treated with G* peptide (10 mg/mL) when compared with no treatment (FIG. 18C). In the mouse experiment shown in FIGS. 18A and 18B, plasma LPA levels were significantly reduced in mice receiving G* peptide compared with their corresponding control mice P<0.05 (FIG. 18D). Western blot showed the expression of cyclin D1 and cyclin A was lower with G* peptide treatment compared with no treatment (FIG. 18E).

Discussion

There is a significant correlation between lipid metabolism and cancer, and inflammatory oxidative stress has long been thought to be associated with the pathophysiology of cancer (28-30). Lipid oxidation and resulting oxidized lipid-mediated inflammation seem to be common to the etiology of a number of inflammatory diseases (31, 32) implicating a role for lipoproteins in the development and progression of several diseases, including cancer. HDL is recognized as an integral part of the innate immune system. HDL is a complex macromolecule whose functional repertoire includes antioxidant, anti-inflammatory, and antimicrobial activities. Unlike LDL, HDL is a heterogeneous mixture of proteins and lipids, which determine structural and functional integrity of HDL. Several protein/enzyme constituents of HDL including phospholipid transfer protein, cholesterol ester transfer protein, and lecithin cholesterol acyl transferase are important for its formation and maturation, whereas other protein/enzyme constituents such as apolipoprotein A-I (apoA-I), apoJ, and paraoxonase-1 (PON1) confer functional properties on HDL (33). Over the last decade, HDL mimetics have shown extraordinary therapeutic promise in preclinical studies in a number of inflammatory diseases (34-40).

We have recently shown that L-4F and L-5F, 2 apoA-I mimetic peptides, reduced viability and proliferation of mouse ovarian cancer cells (ID-8 cells) and cis-platinum-resistant human ovarian cancer cells, and decreased ID-8 cell-mediated tumor burden in C57BL/6J mice when administered subcutaneously or orally (17). We further showed that apoA-I mimetic peptides inhibit tumorigenesis by (i) inhibiting angiogenesis (23) and (ii) inducing expression and activity of MnSOD (41). Because angiogenesis and redox pathways are common features of many cancers, we examined the effect of 2 HDL mimetics, apoA-I mimetic peptide L-4F and an apoJ mimetic peptide G* (42), in the development and progression of colon cancer. Consistent with our hypothesis, our results showed that HDL mimetics inhibit the development of colon cancer generated by injecting CT26 cells into immunocompetent BALB/c mice. Furthermore, we show here for the first time using the mouse model of FAP ($APC^{min/+}$) that oral administration of HDL mimetics is able to suppress the spontaneous development of colon cancer in a mouse model.

There have been 2 sets of clinical trials using the 4F peptides. Bloedon and colleagues (43) found that administration of doses of 4F orally of 4.3 and 7.14 mg/kg significantly improved HDL ant-inflammatory properties despite very low plasma levels (8-16 ng/mL). Bloedon and colleagues (43) also found that administering doses of peptide of 0.43 and 1.43 mg/kg were not effective. Watson and colleagues (44) targeted plasma levels and L-4F was administered daily by either intravenous infusion for 7 days or subcutaneously for 28 days in patients with coronary heart disease. Using a dose of 0.43 mg/kg, Watson and colleagues (44) achieved very high plasma levels but did not achieve any improvement in HDL anti-inflammatory properties. It was concluded that the doses needed for improving HDL function in humans maybe much higher than those used by Watson and colleagues (44) and at least as high as those used by Bloedon and colleagues (43). Recently, Navab and colleagues (45) reported that the dose of the HDL mimetic peptide 4F that was administered, and not the plasma level achieved, determines efficacy and the intestine maybe a major site of action for the peptide regardless of the route of administration. Our results show that the HDL mimetics are effective whether given orally or subcutaneously in mouse models at doses greater than those used by Bloedon and colleagues (43). Given our results with HDL mimetics in mouse colon cancer models and the results of Navab and colleagues (45) indicating that dose determines efficacy and not plasma levels, it will be important to test the high doses used here in any future clinical trials.

One of the downstream targets for the general mechanism of anti-tumorigenic activity of HDL mimetics seems to be angiogenesis, as seen by the reduction in CD31 staining in treated tumors. LPA plays an important role in inflammation, angiogenesis, and cancer, and has become a promising target for therapy (46). Moreover, consistent with our previous findings (17, 23) and current findings, the binding and removal of proinflammatory/proangiogenic lipids such as LPA may be a major part of the mechanism of action for the HDL mimetics.

In conclusion, the results show that HDL mimetics inhibit both induced and spontaneous colon cancer development in mice. The binding and removal of protumorigenic lipids by HDL mimetic peptides likely alters the proliferation capacity of the tumor cells as well asangiogenesis associated with the tumors. Identifying the target lipid(s) is an important next step in delineating the specific mechanism of action for these HDL mimetics.

References

A complete list of citations to references provided throughout Example 5 (identified with numerals in parentheses) can be found in Su et al., 2012, *Mol. Cancer Ther.* 11(6):1311-1319.

Example 6

Figure 19:
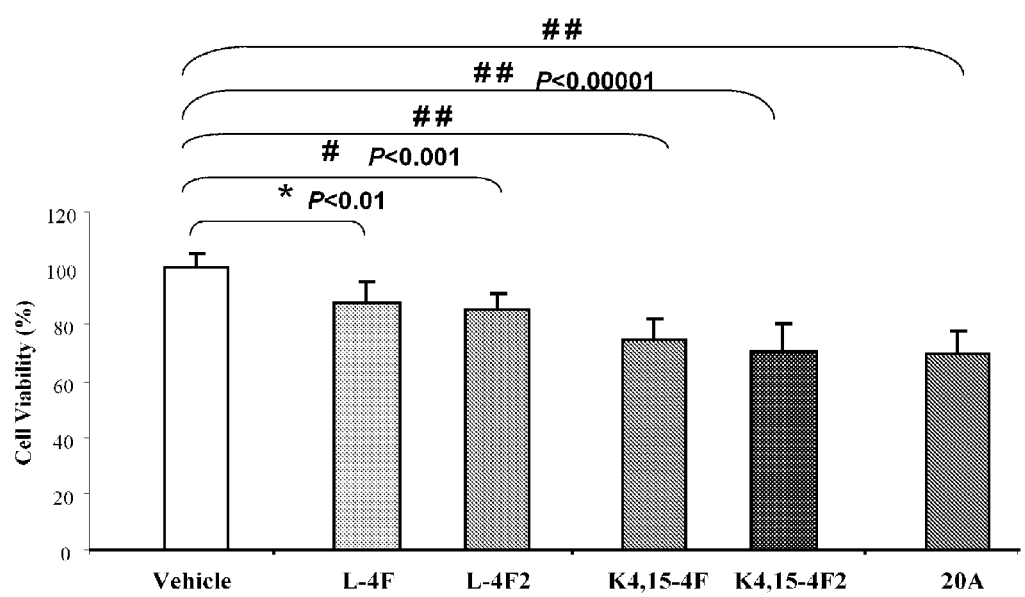
FIG. 19. CT26 cells treated in vitro with various HDL mimetic peptides exhibit reduced cell viability (per MTS assay) within 48 hours of treatment as compared to vehicle-treated controls. The HDL mimetics assayed were L-4F, L-4F2, K4,15-4F, K4,15-4F2, and the 20 amino acid peptide formed from ApoE and G*, LRKLRKRLLR LVGRQLEEFL (SEQ ID NO: 1).

Additional HDL Mimetics Inhibit Tumor Growth and Development in Mouse Model of Colon Cancer This example demonstrates that CT26 cells treated in vitro with various HDL mimetic peptides exhibit reduced cell viability (per MTS assay described above) within 48 hours of treatment as compared to vehicle-treated controls (FIG. 19). The HDL mimetics assayed were L-4F (SEQ ID NO: 12), L-4F2 (SEQ ID NO: 14), K4,15-4F (SEQ ID NO: 27), K4,15-4F2 (SEQ ID NO: 28), and a novel 20 amino acid peptide ("20AA"), LRKLRKRLLR LVGRQLEEFL (SEQ ID NO: 1). The K4,15-4F (SEQ ID NO: 27) and K4,15-4F2 (SEQ ID NO: 28) peptides were based on the K14,15 peptides described in Nayyar et al., 2012, J. Lipid Res. 53(5):849-58, in which the lysines are substituted with arginines at residues 4 and 15, with the latter, K4,15-4F2, further modified to introduce the Aib substitution for alanine at positions 11 and 17. The novel 20 amino acid peptide was formed from peptides of ApoE and G* to create the peptide: LRKLRKRLLR LVGRQLEEFL (SEQ ID NO: 1).

Figure 20:
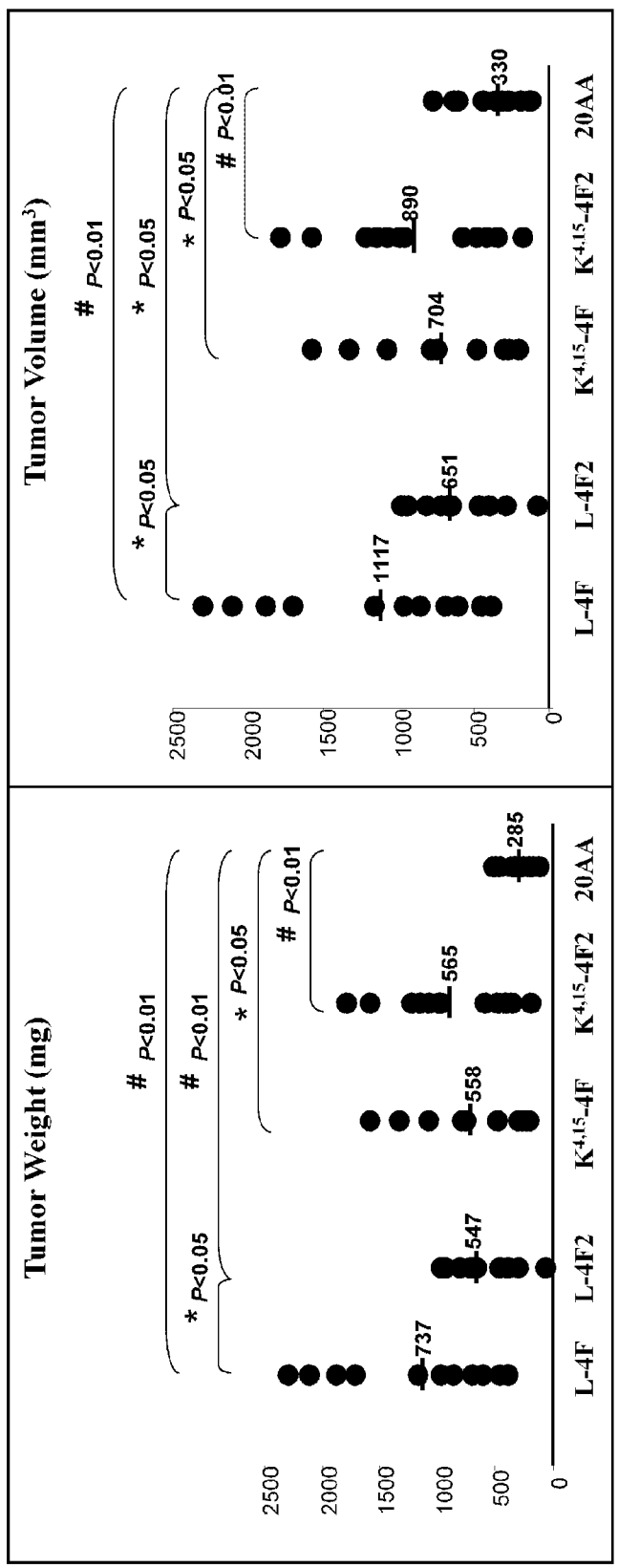
FIG. 20. BALB/c mice that received subcutaneous flank injections of CT26 cells and were subsequently treated with subcutaneous HDL mimetic peptides showed significant reductions in tumor weight (left panel) and tumor volume (right panel).

In addition, BALB/c mice that received subcutaneous flank injections of CT26 cells and were subsequently treated with subcutaneous HDL mimetic peptides showed significant reductions in tumor weight and tumor volume (FIG. 20). These results confirm that a broad class of HDL mimetics can be used in the treatment of cancer.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of inhibiting epithelial tumor growth, the method comprising contacting epithelial tumor cells with an HDL-related molecule selected from the group consisting of HDL mimetic peptides SEQ ID NOs: 1 and 3-9.

2. A method of treating or inhibiting development of epithelial cancer in a subject, the method comprising administering to the subject an HDL-related molecule selected from the group consisting of HDL mimetic peptides SEQ ID NOs: 1 and 3-9.

3. The method of claim 2, wherein the HDL mimetic peptide is administered as an oral supplement.

4. The method of claim 2, wherein the HDL mimetic peptide is SEQ ID NO: 1.

5. The method of claim 2, wherein the subject is mammalian.

6. The method of claim 5, wherein the subject is human.

7. The method of claim 2, wherein the HDL mimetic peptide is SEQ ID NO: 7.

8. The method of claim 1, wherein the HDL mimetic peptide is SEQ ID NO: 1.

9. The method of claim 1, wherein the HDL mimetic peptide is SEQ ID NO: 7.

10. The method of claim 2, wherein the HDL mimetic peptide is administered subcutaneously.

11. The method of claim 2, wherein the epithelial cancer is cancer of the vagina, vulva, ovaries, cervix, uterus, prostate, colon, breast, pancreas, lung, skin, brain, or gastric cancer.

* * * * *